United States Patent
Scheffold et al.

(10) Patent No.: US 9,770,495 B2
(45) Date of Patent: Sep. 26, 2017

(54) **IMMUNOGENIC ANTIGENS FROM *ASPERGILLUS FUMIGATUS***

(71) Applicants: Miltenyi Biotec GmbH, Bergisch-Gladbach (DE); Leibniz Institute for Natural Product Research and Infection Biology—Hans Knoll Institute (HKI), Jena (DE)

(72) Inventors: Alexander Scheffold, Berlin (DE); Petra Bacher, Berlin (DE); Olaf Kniemeyer, Jena (DE); Janka Teutschbein, Jena (DE); Axel Brakhage, Weimar (DE)

(73) Assignees: MILTENYI BIOTEC GMBH, Bergisch-Gladbach (DE); Leibniz Institute for Natural Product Research and Infection Biology—Hans Knoll Institute, Jena (DE)

( * ) Notice: Subject to any disclaimer, the term of this patent is extended or adjusted under 35 U.S.C. 154(b) by 0 days.

(21) Appl. No.: 14/824,957

(22) Filed: Aug. 12, 2015

(65) Prior Publication Data
US 2016/0047809 A1    Feb. 18, 2016

(30) Foreign Application Priority Data

Aug. 15, 2014 (EP) .................................. 14181113

(51) Int. Cl.
*A61K 39/00*  (2006.01)
*G01N 33/50*  (2006.01)

(52) U.S. Cl.
CPC ....... *A61K 39/0002* (2013.01); *G01N 33/505* (2013.01); *A61K 2039/57* (2013.01); *G01N 2333/38* (2013.01); *G01N 2333/705* (2013.01)

(58) Field of Classification Search
None
See application file for complete search history.

(56) References Cited

U.S. PATENT DOCUMENTS 7,504,490 B1    3/2009  Weinstock et al.

FOREIGN PATENT DOCUMENTS

| EP | 2 518 504 A1 | 10/2012 |
|---|---|---|
| WO | WO-02/086090 A2 | 10/2002 |
| WO | WO-02/086090 A3 | 10/2002 |

OTHER PUBLICATIONS

Bacher, P. et al. (2013, e-pub. Mar. 11, 2013). "Antigen-Reactive T Cell Enrichment for Direct, High-Resolution Analysis of the Human Naive and Memory Th Cell Repertoire," *J. Immunol.* 190:3967-3976.

Bacher, P. et al. (2014, e-pub. Dec. 4, 2013). "Antigen-Specific Expansion of Human Regulatory T Cells as a Major Tolerance Mechanism Against Mucosal Fungi,". *Mucosal Immunol.* 7:916-928.

Bacher, P. et al. (2014, e-pub. Aug. 29, 2014). "Identification of Immunogenic Antigens from *Aspergillus fumigatus* by Direct Multiparameter Characterization of Specific Conventional and Regulatory $CD4^+$ T Cells," *The Journal of Immunology* 193(7):3332-3343.

Frentsch, M.. et al. (2005, e-pub. Sep. 25, 2005). "Direct Access to $CD4^+$ T Cells Specific for Defined Antigens According to CD154 Expression," *Nat. Med.* 11:1118-1124.

Hebart, H. (Dec. 15, 2002, e-pub. Aug. 1, 2002). "Analysis of T-cell responses to *Aspergillus fumigatus* Antigens in Healthy Individuals and Patients With Hematologic Malignancies," *Blood* 100(13):4521-4528.

Jolink, H. et al. (Sep. 1, 2013, e-pub. May 22, 2013). "Characterization of the T-Cell-Mediated Immune Response Against the *Aspergillus fumigatus* Proteins Crf1 and Catalase 1 in Healthy Individuals," *The Journal of Infectious Diseases* 208(5):847-856.

Jolink, H. et al. (Apr. 18, 2014). "Induction of *A. fumigatus*-Specific CD4-positive T cells in Patients Recovering From Invasive Aspergillosis", *Haematologica* 99(7):1255-1263.

Schoenbrunn, A. et al. (2012, e-pub. Nov. 16, 2012). "A Converse 4-1BB and CD40 Ligand Expression Pattern Delineates Activated Regulatory T Cells (Treg) and Conventional T Cells Enabling Direct Isolation of Alloantigen-Reactive Natural $Foxp3^+$ Treg,". *J Immunol.* 189:5985-5994.

Shi, L-N. et al. (2012). Immunoproteomics Based Identification of Thioredoxin Reductase GliT and Novel *Aspergillus fumigatus* Antigens for serologic Diagnosis of Invasive Aspergillosis, *BMC Microbiol.* 12(11):1-9.

Vödisch, M.D. et al. (2009). Two-Dimensional Proteome Reference Maps for the Human Pathogenic Filamentous Fungus *Aspegillus fumigatus, Proteomics* 9:1407-1415.

*Primary Examiner* — Brian J Gangle
(74) *Attorney, Agent, or Firm* — Morrison & Foerster LLP

(57) ABSTRACT

The present invention provides the in-vitro use of at least one in-vivo-target antigen of *Aspergillus fumigatus* for selective activation, detection and/or analysis of *Aspergillus fumigatus* specific $CD4^+$ T cells in a sample comprising cells, wherein said at least one in-vivo-target antigen reveals an immune reactivity characterized by i) the in vivo existence of antigen-specific T cells comprising more than 60% memory T cells and ii) said antigen-specific T cells further comprise T cells able to produce IFN-gamma upon stimulation at a frequency between 15% and 80% and/or IL17 upon stimulation at a frequency between 5% and 30%. Said at least one in-vivo-target antigen may be selected from the group consisting of antigens Scw4, Pst1, Shm2, GliT and TpiA or fragments thereof. Also provided are a method, a composition, and a kit thereof.

6 Claims, 10 Drawing Sheets

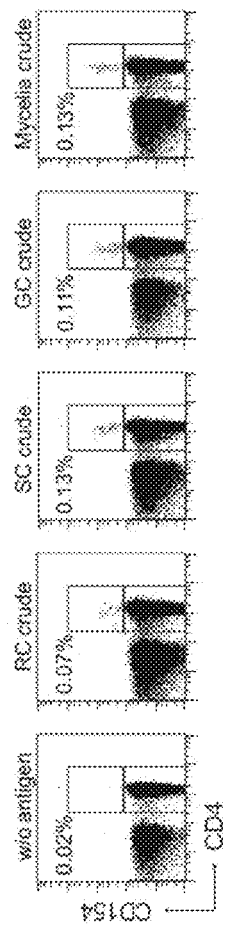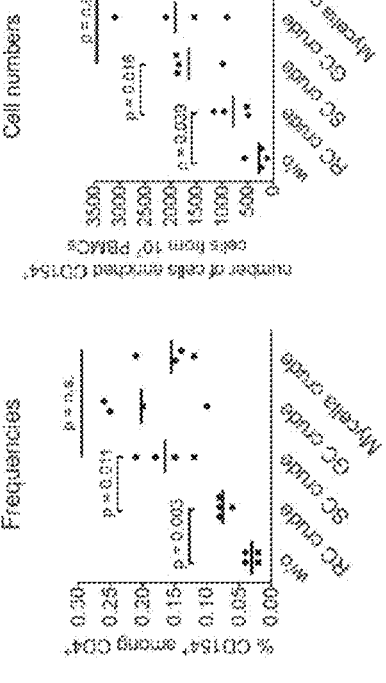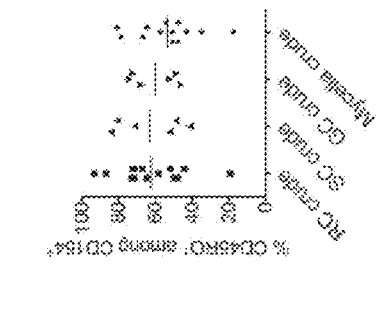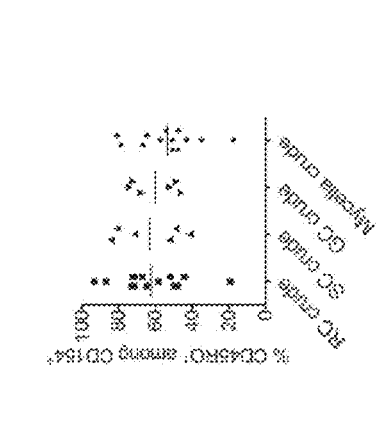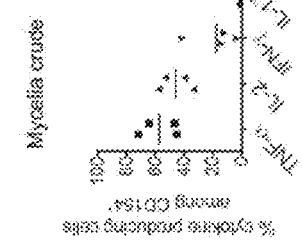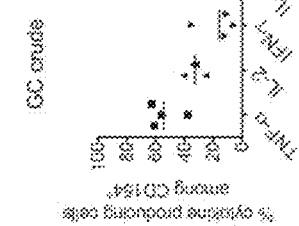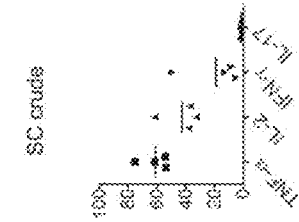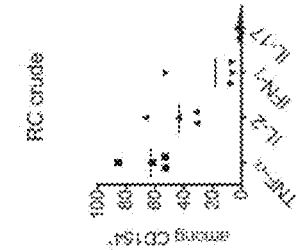
FIG. 1A
FIG. 1B
FIG. 1C
FIG. 1D
FIG. 1E

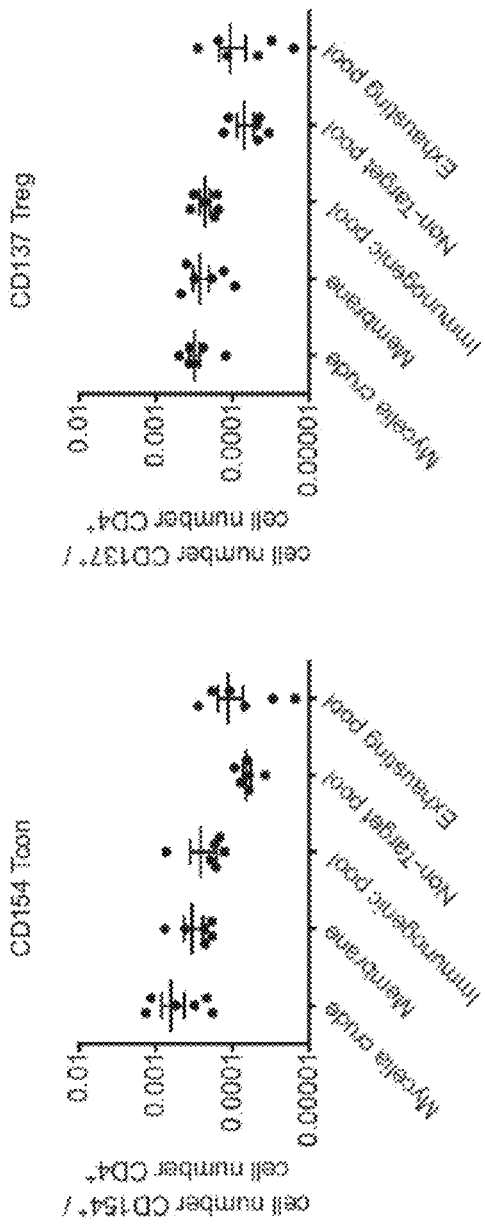
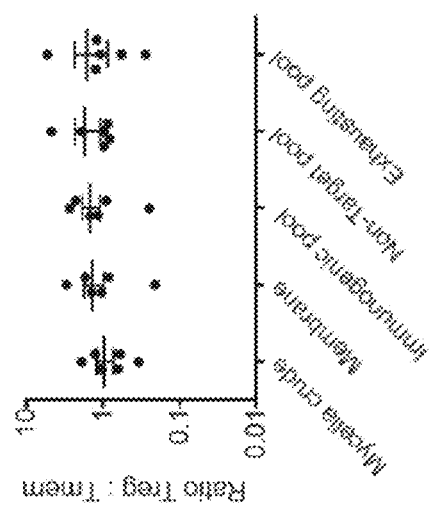
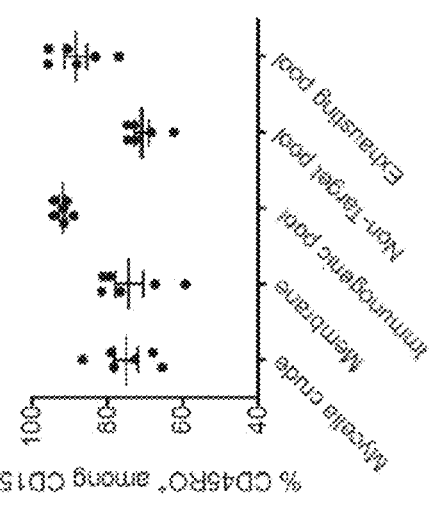
FIG. 5B
FIG. 5C
FIG. 5D

SEQUENCE LISTING

<160> NUMBER OF SEQ ID NOS: 5

<210> SEQ ID NO 1
<211> LENGTH: 369
<212> TYPE: PRT
<213> ORGANISM: Aspergillus fumigatus
<220> FEATURE:
<223> OTHER INFORMATION: cell wall glucanase Scw4

<400> SEQUENCE: 1

```
Met Arg Leu Lys Val Asn Leu Leu Ala Leu Leu Ala Tyr Arg Ser
1               5                   10                  15

Ala Ala His Pro His Val Gly His Arg Arg Asn Ala Glu His Asp Val
                20                  25                  30

Lys Pro Lys Glu Gln Val Ile Val Trp Val Asp His Ala Gly His Thr
            35                  40                  45

Ile Gly Ile Glu His Lys His Gln Thr Pro Thr Ala Thr Phe Lys Ser
50                  55                      60

Ser Pro Thr Glu Leu Pro Leu Leu Pro Asn Thr Asp Asn Ile Ile Pro
65                  70                  75                  80

Asp Asn Pro Leu Pro Lys Leu Thr Val Glu Val Pro Glu Leu Asn Thr
                85                  90                  95

Asn Arg Gly Pro Arg Phe Gly Ile Thr Tyr Ser Pro Tyr Thr Ser His
            100                 105                 110

Gly Thr Cys Lys Thr Phe Asp Gln Ile Asn Gln Asp Ile Glu His Leu
        115                 120                 125

Arg His His Ala Phe Ile Arg Ile Tyr Gly Ile Asp Cys Asp Gln Thr
    130                 135                 140

Lys Leu Val Thr Gln Ala Ser Arg Gln His Gly Leu Lys Val Phe Ala
145                 150                 155                 160

Gly Val Phe Asp Leu His Asn Phe Pro Asp Ser Leu His Tyr Ile Arg
                165                 170                 175

Asp Ala Ala Thr Ala Ala Gly Gly Asp Trp Ser Ile Phe His Thr Ile
            180                 185                 190

Ala Ile Gly Asn Glu Leu Val Asn Lys Gly Gln Asn Lys Pro Ala Asp
        195                 200                 205

Val Val Asn Ala Val Asn Thr Ala Arg Gly Ile Leu Arg Gly Ala Gly
    210                 215                 220

Tyr Gln Gly Pro Val Val Thr Val Asp Thr Phe Ser Val Met Leu Gln
225                 230                 235                 240

His Pro Glu Leu Cys Ala Ala Ser Asp Tyr Cys Ala Ala Asn Cys His
                245                 250                 255

Ala Phe Phe Asp Asn Asn Gln Leu Pro Glu Thr Ala Gly Glu Tyr Ala
            260                 265                 270

Leu Asp Lys Ala Arg Arg Ile Ser Ala Ala Gly Gly Lys Lys Thr
        275                 280                 285

Val Ile Thr Glu Ser Gly Trp Pro His Ala Gly Gln Pro Asn Gly Arg
    290                 295                 300

Ala Val Pro Ser Pro Glu Asn Gln Lys Lys Ala Ile Ala Ser Leu Arg
305                 310                 315                 320

Lys Ala Phe Ala Asp Asp Pro Asp Leu Val Leu Phe Thr Ala Phe Asp
                325                 330                 335

Asp Leu Trp Lys Ser Asp Asn Gln Trp Thr Phe Gly Ala Glu Arg Phe
            340                 345                 350
```

Trp Gly Ile Gln Asp Met Gly Arg Glu Arg Glu Arg Glu Gln Asp Arg
            355                 360                 365

Glu

<210> SEQ ID NO 2
<211> LENGTH: 406
<212> TYPE: PRT
<213> ORGANISM: Aspergillus fumigatus
<220> FEATURE:
<223> OTHER INFORMATION: Pst1

<400> SEQUENCE: 2

Met Arg Pro Leu Phe Phe Cys Leu Leu Leu Ala Leu Arg Leu Val Ala
1               5                   10                  15

Ala Asp Asp Gly Glu Glu Ser Asp Ser Asn Pro Arg Cys Asn Thr Asp
            20                  25                  30

Val Asn Ile Ala Ser Gln Ala Asp Ala Asp Ser Ile Ala Ser Cys His
        35                  40                  45

Thr Val Arg Gly Ser Val Thr Met Ala Ser Ser Val Ser Gly Ala Val
    50                  55                  60

Asn Leu His Gly Val Glu Thr Ile Gln Gly Pro Leu Thr Ala Arg Gly
65                  70                  75                  80

Ala Ser Asp Leu Ser Ala Leu Ile Ala Ser Asp Leu Lys Thr Ile Thr
                85                  90                  95

Gly Thr Leu Thr Val Ala Asn Asn Asp Ala Leu Asn Gln Ile Ser Met
            100                 105                 110

Ser Asn Leu Gln Thr Val Gly Gly Asp Phe Lys Val Glu Asn Asn Arg
        115                 120                 125

Asn Leu Lys Asp Leu Ser Leu Ser Asp Leu Asp Glu Ile Arg Gly Gly
    130                 135                 140

Val Thr Val Ser Asp Leu Thr Arg Arg Ile Ser Leu Ser Asn Leu
145                 150                 155                 160

Asp Thr Val Trp Gly Pro Thr Val Ile His Ser Ser Gly Thr Phe Asn
                165                 170                 175

Cys Ser Ser Leu Asp Ser Lys Leu Ser Gly Glu Asp Arg Val Phe Gln
            180                 185                 190

Ser Ser Tyr Ser Cys Thr Thr Gly Lys Ser Asn Lys Ser Ser Gly Ser
        195                 200                 205

Asp Gly Leu Ser Thr Gly Ala Lys Ala Gly Ile Ala Val Ala Val Val
    210                 215                 220

Ile Val Val Leu Leu Ile Leu Phe Phe Leu Trp Leu Leu Ile Arg Arg
225                 230                 235                 240

Arg Lys Arg Gln Gln Asn Arg Arg Thr Glu Lys Thr Val Thr Asp Ala
                245                 250                 255

Ile Ala Ser Gln Thr Pro Ala Pro Thr Gly His Glu Ser Asn Thr Glu
            260                 265                 270

Lys Leu Thr Ser Thr Leu Thr Pro Gln Glu Asp Val Glu Arg Gly
        275                 280                 285

Ile Pro Arg Lys Pro Val Ser Pro Pro Ala Asp Arg Arg Ser
    290                 295                 300

Ser Val Pro Ala Ser Leu Leu Pro Gly Ser Gly Arg Leu Ser Val Pro
305                 310                 315                 320

Val Ser Leu Leu Pro Gly Ser Asn Pro Ser Val Ser Ser Ala Ser Ala
                325                 330                 335

```
Ser His Arg Arg Val Thr Ser Asp Pro Ser Leu Phe Leu His His Ile
            340                 345                 350

Ala Pro Ser Ala Pro Gln Pro Pro Ser Glu Ile Asp Val Pro Met
            355                 360                 365

Leu Asp Ser Gly Asn Val Tyr Glu Val Gly Asn Asp Arg Thr Arg Pro
370                 375                 380

Gln Thr Pro Ile Tyr Glu Leu Asp Gly Gly Met Ser Asn His Gln
385                 390                 395                 400

Gln Pro Ile His Arg Glu
            405

<210> SEQ ID NO 3
<211> LENGTH: 471
<212> TYPE: PRT
<213> ORGANISM: Aspergillus fumigatus
<220> FEATURE:
<223> OTHER INFORMATION: Shm2

<400> SEQUENCE: 3

Met Ala Thr Tyr Ala Leu Ser Gln Ala His Arg Glu Gln Met Glu Lys
1               5                   10                  15

Ser Leu Val Asp Ser Asp Pro Glu Ile Ala Gln Ile Met Glu Lys Glu
            20                  25                  30

Ile Gln Arg Gln Arg Glu Ser Ile Leu Leu Ile Ala Ser Glu Asn Val
        35                  40                  45

Thr Ser Arg Ala Val Phe Asp Ala Leu Gly Ser Pro Met Ser Asn Lys
50                  55                  60

Tyr Ser Glu Gly Tyr Pro Gly Ala Arg Tyr Tyr Gly Asn Gln His
65                  70                  75                  80

Ile Asp Ala Ile Glu Leu Thr Cys Gln Ala Arg Ala Leu Lys Ala Phe
                85                  90                  95

Asn Leu Asp Pro Glu Lys Trp Gly Val Asn Val Gln Cys Leu Ser Gly
            100                 105                 110

Ser Pro Ala Asn Leu Glu Val Tyr Gln Ala Leu Met Arg Pro His Asp
        115                 120                 125

Arg Leu Met Gly Leu Asp Leu Pro His Gly His Leu Ser His Gly
        130                 135                 140

Tyr Gln Thr Pro Ser Arg Lys Ile Ser Ala Val Ser Thr Tyr Phe Glu
145                 150                 155                 160

Thr Phe Pro Tyr Arg Val Asn Thr Glu Thr Gly Ile Ile Asp Tyr Asp
                165                 170                 175

Thr Leu Glu Ala Asn Ala Glu Leu Tyr Arg Pro Lys Cys Leu Val Ala
            180                 185                 190

Gly Thr Ser Ala Tyr Cys Arg Leu Ile Asp Tyr Gly Arg Met Arg Lys
        195                 200                 205

Ile Ala Asp Lys Val Gly Ala Tyr Leu Ile Val Asp Met Ala His Ile
210                 215                 220

Ser Gly Leu Val Ala Ala Gly Val Ile Pro Ser Pro Phe Glu Tyr Ala
225                 230                 235                 240

Asp Val Val Thr Thr Thr Thr His Lys Ser Leu Arg Gly Pro Arg Gly
                245                 250                 255

Ala Met Ile Phe Phe Arg Lys Gly Val Arg Ser Thr Asp Pro Lys Thr
            260                 265                 270

Gly Lys Glu Ile Met Tyr Asp Leu Glu Gly Pro Ile Asn Phe Ser Val
        275                 280                 285
```

-continued

Phe Pro Gly His Gln Gly Gly Pro His Asn His Thr Ile Thr Ala Leu
    290             295                 300

Ala Val Ala Leu Lys Gln Ala Ala Thr Pro Glu Phe Arg Gln Tyr Gln
305             310                 315                 320

Glu Gln Val Leu Lys Asn Ala Lys Ala Leu Glu Val Glu Phe Lys Ala
                325                 330                 335

Leu Gly His Lys Leu Val Ser Asp Gly Thr Asp Ser His Met Val Leu
            340                 345                 350

Leu Asp Leu Arg Pro Lys Gly Leu Asp Gly Ala Arg Val Glu Ala Val
        355                 360                 365

Leu Glu Gln Ile Asn Ile Ala Cys Asn Lys Asn Ser Ile Pro Gly Asp
370                 375                 380

Lys Ser Ala Leu Thr Pro Cys Gly Ile Arg Ile Gly Thr Pro Ala Met
385                 390                 395                 400

Thr Ser Arg Gly Met Ser Glu Glu Asp Phe Lys Arg Val Ala Arg Tyr
                405                 410                 415

Ile Asp Gln Val Ile Asn Leu Cys Lys Ser Ile Gln Ala Asp Leu Pro
            420                 425                 430

Lys Glu Ala Asn Lys Leu Lys Asp Phe Lys Ala Lys Val Ala Ser Gly
        435                 440                 445

Ser Val Pro Glu Ile Leu Ala Leu Arg Lys Glu Val Ala Glu Trp Ala
450                 455                 460

Ser Thr Tyr Pro Leu Pro Val
465                 470

<210> SEQ ID NO 4
<211> LENGTH: 334
<212> TYPE: PRT
<213> ORGANISM: Aspergillus fumigatus
<220> FEATURE:
<223> OTHER INFORMATION: GliT

<400> SEQUENCE: 4

Met Ser Ile Gly Lys Leu Leu Ser Asn Gly Ala Leu Leu Val Asp Val
1               5                   10                  15

Leu Ile Ile Gly Ala Gly Pro Ala Gly Leu Ser Thr Ala Thr Gly Leu
            20                  25                  30

Ala Arg Gln Leu His Thr Ala Val Val Phe Asp Ser Gly Val Tyr Arg
        35                  40                  45

Asn Ala Lys Thr Gln His Met His Asn Val Leu Gly Trp Asp His Arg
50                  55                  60

Asn Pro Ala Glu Leu Arg Ala Ala Gly Arg Ala Asp Leu Thr Thr Arg
65                  70                  75                  80

Tyr Ser Thr Ile Gln Phe Gln Asn Ser Thr Ile Glu Ala Ile Arg Gln
                85                  90                  95

Val Glu Thr Asn Gln Leu Phe Glu Ala Arg Asp Asn Glu Gly His Ser
            100                 105                 110

Trp Tyr Gly Arg Lys Val Val Leu Ala Thr Gly Val Arg Asp Ile Pro
        115                 120                 125

Leu Asp Ile Glu Gly Tyr Ser Glu Cys Trp Ala Asn Gly Ile Tyr His
130                 135                 140

Cys Leu Phe Cys Asp Gly Tyr Glu Glu Arg Gly Gln Glu Thr Val Gly
145                 150                 155                 160

Val Leu Ala Leu Gly Pro Ile Ala Asn Pro Ala Arg Ala Leu His Leu
                165                 170                 175

```
Ala Arg Met Ala Leu Arg Leu Ser Glu Ser Val Thr Ile Tyr Thr Asn
            180                 185                 190

Gly Asn Glu Gln Leu Ala Lys Glu Ile Gln Gln Ala Ala Glu Glu Ser
        195                 200                 205

Pro Val Gly Ala Ser Gly Leu Lys Phe Glu Ala Arg Pro Ile Arg Arg
    210                 215                 220

Phe Glu Lys Gly Asp Val Ala Lys Thr Val Ile Val His Leu Gly Glu
225                 230                 235                 240

Ser Glu Ser Lys Thr Glu Gly Phe Leu Val Tyr Asn Pro Gln Thr Glu
                245                 250                 255

Val Asn Gly Pro Phe Ala Lys Gln Leu Ala Leu Asn Met Thr Glu Gly
            260                 265                 270

Gly Asp Ile Leu Thr Thr Pro Pro Phe Tyr Glu Thr Ser Val Pro Gly
        275                 280                 285

Val Phe Ala Val Gly Asp Cys Ala Thr Pro Leu Lys Ala Val Thr Pro
    290                 295                 300

Ala Val Ser Met Gly Ser Leu Ala Ala Gly Gly Leu Val Ala Gln Leu
305                 310                 315                 320

Gln Ala Gln Ala Leu Pro Glu Phe Arg Leu Asp Gln Glu Leu
                325                 330

<210> SEQ ID NO 5
<211> LENGTH: 249
<212> TYPE: PRT
<213> ORGANISM: Aspergillus fumigatus
<220> FEATURE:
<223> OTHER INFORMATION: TpiA

<400> SEQUENCE: 5

Met Pro Arg Gln Phe Phe Val Gly Gly Asn Phe Lys Met Asn Gly Val
1               5                   10                  15

Thr Asp Thr Ile Thr Ser Ile Val Lys Asn Leu Asn Glu Ala Lys Leu
            20                  25                  30

Asp Pro Ser Val Glu Val Val Ile Ser Pro Ser Ala Leu Tyr Leu Leu
        35                  40                  45

Leu Ala Arg Gln Ala Ala Asp Pro Lys Ile Gly Val Ala Ala Gln Asn
    50                  55                  60

Val Phe Asp Lys Pro Asn Gly Ala Phe Thr Gly Glu Ile Ser Val Glu
65                  70                  75                  80

Gln Leu Lys Asp Ala Lys Ile Asp Trp Val Ile Gly His Ser Glu
                85                  90                  95

Arg Arg Val Ile Leu Lys Glu Thr Asp Glu Phe Ile Ala Arg Lys Thr
            100                 105                 110

Lys Ala Ala Ile Asp Gly Gly Leu Asn Val Ile Leu Cys Ile Gly Glu
        115                 120                 125

Thr Leu Glu Glu Arg Glu Ala Gly Lys Thr Ile Asp Val Val Arg Arg
130                 135                 140

Gln Leu Thr Ala Val Ala Lys Asp Leu Ser Lys Glu Gln Trp Gln Lys
                150                 155                 160
145

Val Val Ile Ala Tyr Glu Pro Val Trp Ala Ile Gly Thr Gly Lys Val
            165                 170                 175

Ala Thr Thr Glu Gln Ala Gln Glu Val His Ala Ala Ile Arg Lys Trp
        180                 185                 190

Leu Ser Asp Asp Val Ser Ala Glu Ala Ser Glu Asn Val Arg Ile Ile
    195                 200                 205
```

-continued

```
Tyr Gly Gly Ser Val Ser Glu Lys Asn Cys Arg Asp Leu Ala Lys Gln
    210             215                 220

Pro Asp Val Asp Gly Phe Leu Val Gly Gly Ala Ser Leu Lys Pro Ala
225             230                 235             240

Phe Val Glu Ile Val Asn Ala Arg Leu
                245
```

IMMUNOGENIC ANTIGENS FROM ASPERGILLUS FUMIGATUS

CROSS REFERENCE TO RELATED APPLICATIONS

This application claims priority to European Application No. EP14181113.3, filed Aug. 15, 2014, the contents of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 212302002900SeqList.txt, date recorded: Aug. 11, 2015, size: 16 KB).

FIELD OF THE INVENTION

The present invention relates generally to in-vivo-target antigens from *Aspergillus fumigatus*, in particular to the use of these antigens for detecting, isolating and/or analyzing *Aspergillus fumigatus*-specific CD4$^+$ T cells; and the use of these antigens as vaccines against *Aspergillus fumigatus* infection or allergy.

BACKGROUND OF THE INVENTION

*Aspergillus fumigatus* (*A. fumigatus*) is a ubiquitous spore-producing mold that can cause a diverse spectrum of human diseases, ranging from allergic hypersensitivity and non-invasive colonization to life-threatening invasive infections. Invasive aspergillosis (IA) is the most devastating disease caused by this fungus in immunocompromised patients. Despite new anti-fungal drugs, morbidity and mortality continue to be unacceptable high and invasive aspergillosis has become a major cause of infection-related mortality in hematopoietic stem cell recipients.

Although we routinely inhale several hundreds or thousands of *A. fumigatus* conidia per day, immune-competent individuals are efficiently protected by innate and adaptive immune mechanisms. Lung-resident alveolar macrophages and neutrophils ingest and kill *A fumigatus* conidia and germlings and recruit other immune cells by secretion of pro-inflammatory cytokines. There is increasing evidence that CD4$^+$ T cells orchestrate the anti-fungal immune response. In mouse models, monocytes and dendritic cells have been shown to prime *A. fumigatus*-specific CD4$^+$ T cell responses that migrate to the airways. Adoptive transfer of *A. fumigatus*-specific IFN-γ producing T cells protected mice from invasive fungal disease and correlated with survival of IA patients. In accordance with the idea that humans are constantly confronted with fungal antigens it was recently shown that a small population of *A. fumigatus*-specific T cells is indeed consistently present in healthy donors (Bacher et al J Immunol 2013, Bacher et al Mucosal Immunol 2013). In IA patients, the frequencies of *A. fumigatus*-reactive T cells are strongly increased (unpublished observation) indicating the involvement of specific CD4$^+$ T cells in antifungal immune defense.

Therefore, approaches supporting fungus-specific CD4$^+$ T cells in immuno-compromised persons, e.g. by vaccination or adoptive T cell transfer seem to be promising for pre-emptive or therapeutic intervention against invasive fungal infections. However, in order to develop efficient immunotherapies or immunodiagnostic tools, a crucial first step is to define the antigen specificity of the human CD4$^+$ T cells in vivo. Due to the complexity of the *A. fumigatus* proteome it is currently not known against which fungal antigens human T cells predominantly react and which T cell specificities are protective. The *A. fumigatus* genome contains several thousand open reading frames, encoding potential antigenic proteins. Bacher et al (J Immunol 2013 & Mucosal Immunol 2013) disclosed a highly specific and sensitive assay to enumerate and characterize antigen-specific CD4$^+$ T cells directly ex vivo based on CD154$^+$pre-enrichment (Antigen-Reactive T cell Enrichment, ARTE). There is a need in the art for the identification of immunogenic antigens of *Aspergillus fumigatus* allowing the detection of *Aspergillus fumigatus*-specific T cells and/or which are useful for immunotherapy or immunodiagnostics.

SUMMARY OF THE INVENTION

Using the ARTE technology, we were able to identify very rare *Aspergillus fumigatus* specific T cells in all healthy donors, in accordance with the idea that humans are continuously exposed to fungal spores. Interestingly we found that using the complete *Aspergillus* lysate as an antigen, which covers most fungal proteins a large part of the reactive T cells had a naive phenotype. This data suggested that *Aspergillus* per se may not induce strong T cell responses in healthy individuals leaving most T cells untouched in a naive state. Surprisingly a completely different picture emerged, when we analysed a set of recombinant proteins from *A. fumigatus*, which were either known as immunogenic proteins or newly identified as strongly expressed by *A. fumigatus* and/or as target of specific antibodies in sera from patients with invasive Aspergillosis.

Surprisingly, our analysis identified from the large proteome of *A. fumigatus* several new in vivo target proteins, including Scw4, Pst1, Shm2, GliT and TpiA that have not been described as human T cell targets before. These five proteins belong to the "immunogenic" protein group. Said immunogenic proteins Scw4, Pst1, Shm2, GliT and TpiA are characterized by i) the in vivo existence of antigen-specific T cells containing more than 60% memory T cells and ii) said antigen-specific T cells further contain T cells able to produce IFN-gamma upon stimulation at a frequency between 15% and 80% and/or IL17 upon stimulation at a frequency between 5% and 30%.

These proteins can be used as in-vivo-target antigens to measure the magnitude and/or the quality of the T cell response against *A. fumigatus* in healthy persons or persons with *A. fumigatus* related diseases, i.e. invasive Aspergillosis (IA), allergies or allergic bronchopulmonary aspergillosis (ABPA) or *Aspergillus* colonisation of the lung (e.g. in cystic fibrosis patients) via the selective activation of *Aspergillus fumigatus*-specific CD4$^+$ T cells in a blood or tissue sample or via MHC multimers loaded with peptides derived from the in vivo target proteins. In addition, they can be used in a method for detecting, isolating and/or analyzing *Aspergillus fumigatus*-specific CD4$^+$ T cells. The frequency, phenotype or functional characteristics of the specific T cells may be used as a read-out to identify disease associated changes, which might have diagnostic or therapeutic relevance. Pharmaceutical compositions comprising *Aspergillus*-specific CD4+ T cells obtainable by the method of the present invention or comprising an in-vivo-target antigen of *Aspergillus fumigatus* may be used in adoptive cell therapy. Pharmaceutical compositions comprising one or more of the identified proteins or fragments thereof may also be used for vaccination against *Aspergillus* infections or allergies.

BRIEF DESCRIPTION OF THE DRAWINGS

FIG. 1A-FIG. 1E shows memory CD4+ T cells from healthy human donors show specific reactivity against lysates from different *A. fumigatus* growth phases.

Following stimulation of PBMCs with the indicated crude lysates of different morphotypes, CD154+ expression on CD4+ T cells was analyzed directly ex vivo. (FIG. 1A) Cells were gated on lymphocytes and aggregates (scatter area versus height), dead cells and non-T cell lineages (CD14+, CD20+, dump) were excluded. Representative dot plot examples from one donor with frequencies of CD154+ cells among CD4+ lymphocytes and (FIG. 1B) summary of several donors with horizontal lines indicating mean values. (FIG. 1C-FIG. 1E) CD154+ cells were magnetically pre-enriched and stained for cytokine expression and phenotypic markers. (FIG. 1C) Number of CD154+ cells obtained from 1×10E7 stimulated PBMCs. (FIG. 1D) Percentages of cytokine-expressing cells among CD154+ T cells and (FIG. 1E) percentages of CD45RO+ memory cells among CD154+ T cells are shown. Significance was determined using paired Student's t-test. RC=resting conidia; SC=swollen conidia; GC=germinating conidia.

(FIG. 2A) Representative dot plot examples from one donor with percentage of reactive cells gated on CD4+ lymphocytes and (FIG. 2B) statistical analysis of several donors with horizontal lines indicating mean values. (FIG. 2C) The fungal lysate reactive T cell lines were re-stimulated with the specific lysate used for initial stimulation and analyzed for intracellular cytokine expression. Percentages of cytokine producing cells among CD154+ cells are depicted. Significance was determined using paired Student's t-test. RC=resting conidia; SC=swollen conidia; GC=germinating conidia.

(FIG. 3A) Representative dot plot examples from one donor. For an optimal detection of rare CD154+ events, aggregates, dead cells and non-target cells (CD8+, CD14+, CD20+) were excluded by using a dump channel. The numbers of CD154+ cells obtained after enrichment are indicated. (FIG. 3B) Specificity of single protein-reactive CD154+ T cells. PBMCs were stimulated with the indicated proteins. CD154+ cells were isolated, subsequently expanded for 3 weeks and tested for specificity via antigen re-stimulation. Percentage of reactive cells among CD4+ lymphocytes are shown for several donors, as determined by CD154 and TNF-α, expression.

Enriched CD154+ cells were ex vivo analyzed for frequency, expression of CD45RO and pro-inflammatory cytokine production and classified into "immunogenic", "non-target" and "exhausting" proteins, as indicated. Frequency was determined as in FIG. 4, percentages of CD45RO+ memory cells among CD154+ cells and percentages of cytokine-expressing cells among CD154+ T cells are shown. pp=peptide pool; r=recombinant FIG. 5A-FIG. 5D show stimulation of *A. fumigatus* specific Treg with pools of immunogenic, non-target and exhausted proteins. 2×10E7 PBMCs were stimulated with *A. fumigatus* crude mycelia lysate, membrane lysate or the indicated pools of single proteins. CD154+ and CD137+ cells were magnetically enriched and stained for Foxp3 expression. (FIG. 5A) Representative dot plot examples from one donor. Cells are gated on CD4+ CD154+ lymphocytes and Foxp3 expression on CD137+ cells is depicted. The numbers of CD137+ Foxp3+ Treg cells obtained after enrichment are indicated. (FIG. 5B) Enumeration of reactive CD154+ Tcon and CD137+ Treg in several donors (n=6). The total number of CD154+ and CD137+ cells obtained after enrichment was normalized to the total number of CD4+ cells applied to the column. Background enriched from the non-stimulated control was subtracted. (FIG. 5C) Percentages of CD45RO+ memory cells among CD154+ cells (Tmem). (FIG. 5D) Ratio of CD137+ Treg to CD154+ CD45RO+ Tmem.

Figure 2A:
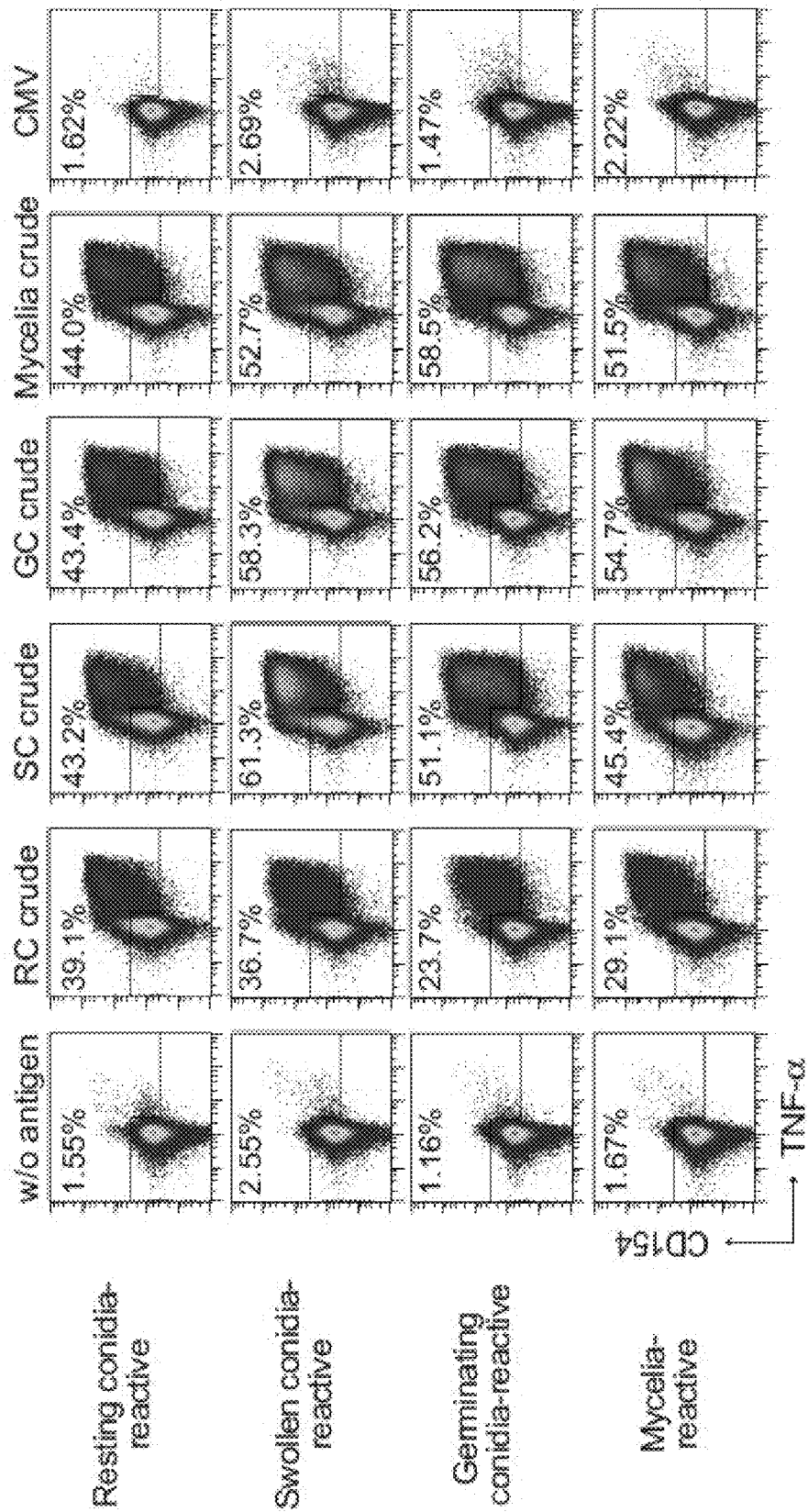
FIG. 2A-FIG. 2C. show resting conidia contain less T cell antigens than other *A. fumigatus* morphotypes. Following stimulation with the different crude growth phase lysates, CD154+ cells were magnetically isolated and expanded for 2 weeks. Upon re-stimulation with and without antigens as indicated, reactive CD4+ T cells were determined by CD154 and TNF-α, expression.
Figure 2B:
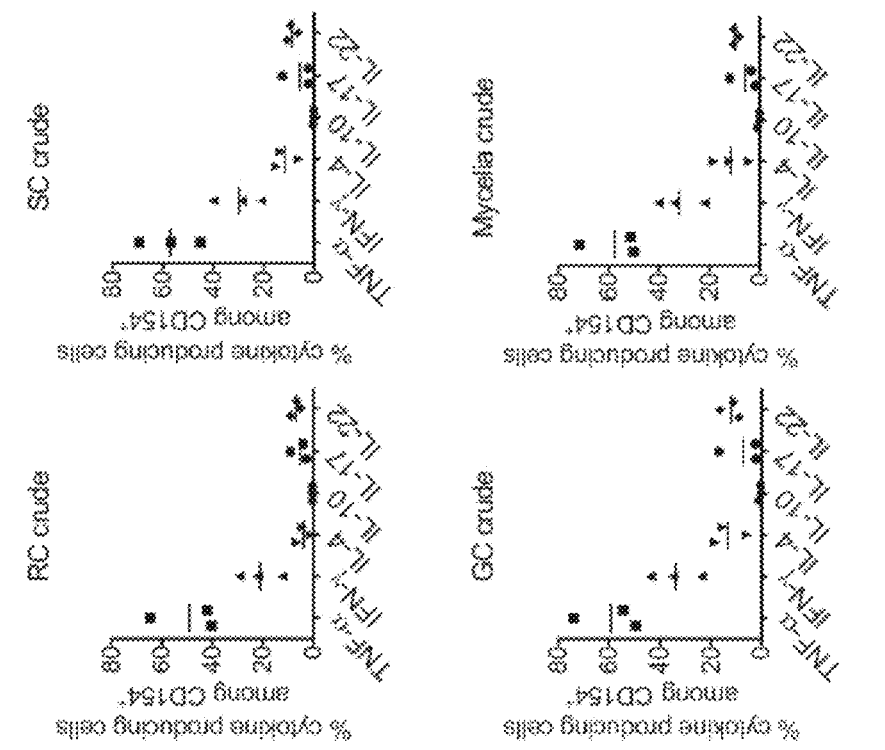
Figure 2C:
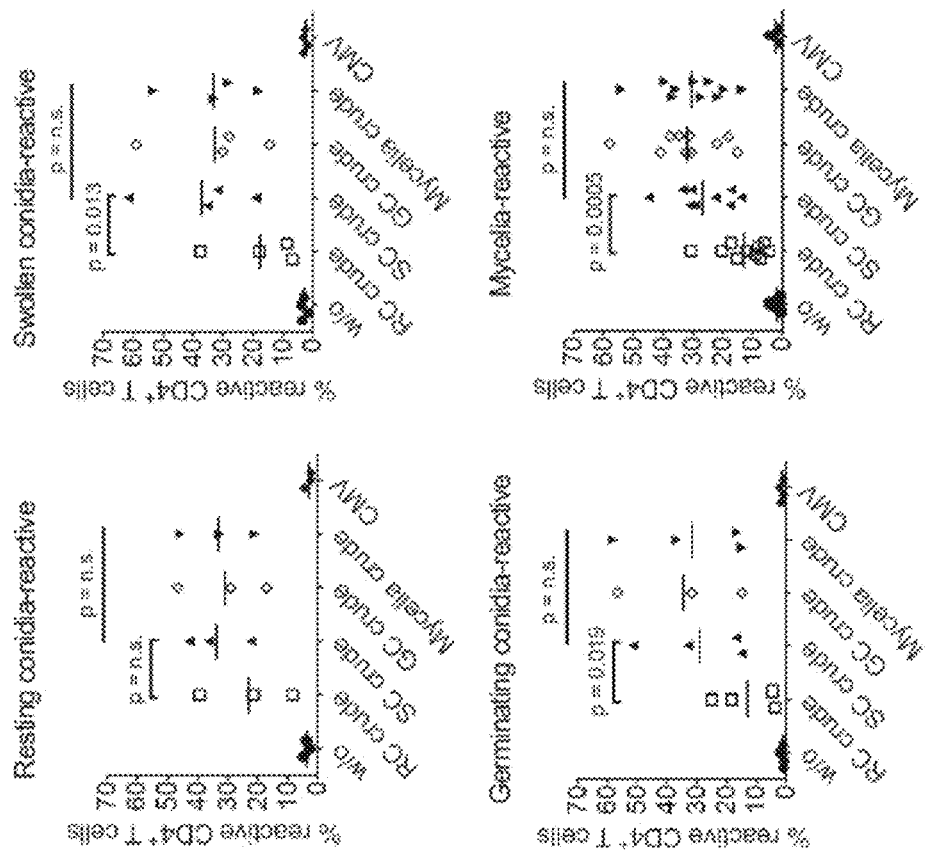

PBMCs were stimulated with *A. fumigatus* crude mycelia lysate or with pools of the proteins classified as immunogenic, non-target and exhausting. Antigen-specific T cells were isolated by ARTE and analyzed for polyfunctional cytokine expression of TNF-alpha, IL-2 and IFN-gamma. Statistical analysis from four donors with indicated mean values are shown.

DETAILED DESCRIPTION OF THE INVENTION

The presence of *A. fumigatus*-specific CD4+ T cells in human blood has been described in several studies, using in vitro stimulation assays with whole conidia and hyphae, crude lysates, single proteins or epitopes. However, it has not been defined yet, which developmental stage (resting, swollen, germinating conidia or mycelia) and which subcellular protein fraction prime *A. fumigatus*-specific T cells in healthy human donors. Here, we demonstrate that the activated developmental stages of the fungus (swollen, germinating conidia and hyphae) contain the largest reservoir of potential T cell epitopes. Furthermore, T cell antigens in the metabolic active *A. fumigatus* morphotypes were largely overlapping, which is in line with recent results on the proteomic signature of *A. fumigatus* during early development. These studies show that the majority of mycelial proteins are also present in all early, metabolically active morphotypes and only the abundance varies.

The method ARTE (Antigen-Reactive T cell Enrichment; Bacher et al J Immunol 2013) was used for the direct quantification and multi-parameter characterization of rare human CD4+ T cells specific for various antigens of the important human pathogenic fungus *Aspergillus fumigatus*. We show that ARTE can be used for the direct quantification and multi-parameter characterization of rare human CD4+ T cells specific for various antigens of the important human-pathogenic fungus *A. fumigatus*. The sensitivity and flexibility of the method enabled the analysis of T cells specific for various developmental stages, subcellular compartments as well as a large set of selected single recombinant proteins. Importantly, the multi-parameter characterization of T cells reactive against single *A. fumigatus* proteins, i.e. the combination of frequencies, naive/memory distribution and effector cytokine production of specific T cells allowed the classification of proteins/antigens of *A. fumigatus* into two groups: the in-vivo-target antigens and the non-target antigens. One group (the non-target antigens) revealed a picture similar to the whole protein lysate, characterized by high frequencies of naive T cells (about 50%) and low frequencies of effector cytokine producers (<20% IFN-gamma, <5% IL-17) in most donors, suggesting that these proteins are no in vivo targets of T cells in healthy donors. The other group (in-vivo-target antigens) revealed a surprisingly high frequency of memory T cells (preferentially more than 60%) and only few naive T cells (preferentially less than 40%), suggesting that proteins of this group are in vivo targets of the T cell response in healthy donors. This group of in vivo targets can further be split up into two subgroups: "Immunogenic" proteins are characterized by high overall T cell frequencies (preferentially more than 1 in 10E3, more preferentially more than 1 in 10E4, most preferentially more than 1 in 10E5), mainly memory type cells (60-100%) and high IFN-$\gamma$ (15-80%) and/or IL-17 (5-30%) production. "Exhausting" proteins were classified due to their low to intermediate overall frequencies (preferentially less than 1 in 10E4, more preferentially less than 1 in 10E5, most preferentially less than 1 in 10E6) and lack of effector cytokine production (<15% IFN-gamma, <5% IL-17), although the majority of cells had a clear memory phenotype (60-100%). These properties may indicate deletion and/or anergy of specific T cells due to overstimulation in vivo again supporting the idea that these proteins are in vivo recognized during in vivo contact with *A. fumigatus*. Thus the "immunogenic" and "exhausting" antigens are defined as "in-vivo-target antigens". Importantly these two subgroups with obvious immune reactivity in vivo contrast with the third group, which we termed "non-target" proteins, since they induce high overall T cell frequencies, but strikingly a large proportion of the cells is still in the naive state and also lacks effector cytokine production. This indicates that no immune reactivity is induced in vivo despite the fact that these proteins can stimulate T cells when present during in vitro stimulation. This suggests that non-target proteins are not relevant for T cell responses against *A. fumigatus* infections in healthy donors. The fact that the T cells reacting against the total *A. fumigatus* lysate also contain many naive T cells shows that indeed a large part of the *A. fumigatus* proteome actually belongs to the non-target protein group, i.e. is immunologically neutral. Thus identification of true in vivo target proteins, as disclosed in the present application, is an important step to identify proteins which possess relevance during in vivo *A. fumigatus* infections and thus possess potential value as diagnostic or therapeutic tools. However it has to be kept in mind that single proteins might be classified into different groups in different donors, indicating that donor-specific features may influence the reactivity against single proteins, e.g. MHC restriction elements.

From the identified immunogenic proteins, Crf1, Sod3 and Aspf22 have previously been described to elicit CD4+ T cell responses in humans. However, our analysis also identified new immunogenic proteins, including Scw4, Pst1, Shm2, GliT and TpiA that have not been described as human T cell targets before. These five new immunogenic proteins as a group are specifically defined by the parameters described above for "immunogenic proteins", i.e. the antigen-specific T cells recognizing these proteins and present in vivo in most healthy donors typically comprise more than 60% memory T cells and they also comprise T cells able to produce IFN-$\gamma$ at frequencies between 15-80% and/or IL-17 at frequencies between 5-30% upon stimulation. The gliotoxin oxidase GliT has recently been identified via an immunoproteome screening approach and has been suggested to represent a novel antigen for serologic diagnosis of aspergillosis (Shi et al, BMC Microbiol 2012). Interestingly also two other "immunogenic" proteins, the enolase Aspf22 and Shm2 were detected in immunoblots using sera from patients with allergic bronchopulmonary aspergillosis. In addition, Shm2 belongs to the most abundant proteins identified in the mycelial proteome (Vodisch et al, Proteomics 2009).

However, it is important to note that the same characteristics also apply to other proteins that were tested in our study, e.g. CpcB, Aspf2 and Aspf3 which all belong to the "exhausting" group. Furthermore CatB, classified by our analysis as a "non-target" protein has previously been described to induce strong T cell proliferation in vitro but vaccination with CatB did not protect mice from invasive aspergillosis. Thus it is obvious, that other factors than protein localization, abundance or antibody reactivity are critical parameters to determine the true in vivo T cell stimulatory capacity and highlights the potential of our approach to systematically predict immunogenic and potential protective target proteins.

In addition to the phenotypic characteristics, ARTE also allows to determine the functionally important production of effector cytokines, such as IFN-$\gamma$ or IL-17. Although IL-17 is frequently claimed as an important cytokine for antifungal immune responses, the importance for protection against fungal infections versus immunopathology is currently under debate. In this study we observed a predominant IFN-$\gamma$ production and only low IL-17, which is in line with previous reports suggesting that *A. fumigatus* elicits predominantly Th1 responses in vivo. Th2 cytokines (IL-4, IL-5, IL-13) were only marginal produced against the defined pools of single proteins (data not shown) and have previously been shown to be typically below 5% of all reactive CD154+ cells against the total soluble lysate (Bacher et al J. Immunol 2013). However, when single proteins or pools thereof were analyzed, polyfunctional cytokine production (co-expression of TNF-$\alpha$, IL-2 and IFN-$\gamma$) and strong IL-17 cytokine production was only observed against proteins classified as "immunogenic". Also against the immunogenic proteins, IFN-$\gamma$ was the dominating lineage defining cytokine confirming also on the level of single proteins that the in vivo response against *A. fumigatus* is rather biased towards a Th1 pattern. Moreover, some proteins (e.g. Scw4, Pst1, GliT, Aspf22) elicited in addition to IFN-$\gamma$ the co-production of relatively high amounts of IL-17. The knowledge about the specific cytokine induction potential of certain proteins may help to improve vaccine design in the future. However, the functional importance of the various T cell cytokines has to be determined beforehand. Interestingly, by pooling proteins according to our classification, we found that not only conventional memory T cells, but also regulatory T cells were strongly activated by the immunogenic proteins, indicating that Tcon and Treg recognize the same antigens. In fact the number of Treg exactly paralleled the number of memory Tcon resulting in a stable Treg/Tmem ratio for all antigens. This indicates that Treg are not selectively generated against a subgroup of proteins but their expansion seems to be coupled to the expansion of conventional T cells, which may be mediated via growth factor supply, such as IL-2. Thus, the T cell response against all *A. fumigatus* proteins is controlled by Treg and therefore the depletion of Treg might be a promising strategy for releasing full T cell responses, e.g. for immunotherapeutic approaches. Alternatively Treg can be used directly ex vivo or following in vitro expansion to treat patients with overshooting or chronic inflammatory or allergic responses against *A. fumigatus*.

Finally, despite the fact that our analysis could define a set of immunogenic *A. fumigatus* proteins, the overall T cell response was directed against a multitude of different proteins. In addition, the T cell frequencies against single antigens were very low and there was significant donor-to-donor variation. This indicates that the *A. fumigatus*-specific T cell response is largely heterogeneous and also determined by host-specific or environmental factors, such as MHC restriction or variability in timing and dosage of antigen exposure. In line with this, a recent study identified 7 and 30 different T cell epitopes within the Crf1 and CatB protein, respectively, which are presented by different HLA-class II molecules. Thus, the existence of a single or even a few immuno-dominant antigens is rather unlikely emphasizing the importance to identify of single proteins or even peptides which are true in vivo targets in individual donors, as demonstrated here.

Therefore in a first aspect the present invention provides the in-vitro use of at least one in-vivo-target antigen of *Aspergillus fumigatus* for selective activation, detection and/or analysis of *Aspergillus fumigatus* specific CD4$^+$ T cells in a sample comprising T cells, wherein said at least one in-vivo-target antigen reveals an immune reactivity characterized by
  i) the in vivo existence of antigen-specific T cells comprising more than 60% memory T cells, and
  ii) said antigen-specific T cells further comprise T cells able to produce IFN-gamma upon stimulation at a frequency between 15% and 80% and/or IL17 upon stimulation at a frequency between 5% and 30%.

Said at least one in-vivo-target antigen may be selected from the group consisting of antigens Scw4, Pst1, Shm2, GliT and TpiA or fragments thereof.

In another aspect the present invention provides a method for detecting, isolating and/or analyzing *Aspergillus fumigatus*-specific CD4$^+$ T cells, the method comprising:
  a) Adding to a sample comprising T cells at least one in-vivo-target antigen of *Aspergillus fumigatus*, wherein said at least one in-vivo-target antigen reveals an immune reactivity characterized by
    i) the in vivo existence of antigen-specific T cells comprising more than 60% memory T cells, and
    ii) said antigen-specific T cells further comprise T cells able to produce IFN-gamma upon stimulation at a frequency between 15% and 80% and/or IL17 upon stimulation at a frequency between 5% and 30%,
  b) Detection, isolation and/or analysis of said *Aspergillus fumigatus*-specific CD4$^+$ T cells.

Said at least one in-vivo-target antigen may be selected from the group consisting of antigens Scw4, Pst1, Shm2, GliT and TpiA or fragments thereof.

Detection and analysis of said *Aspergillus fumigatus*-specific CD4$^+$ T cells may be performed by standard assays known in the field to analyse activated T cells, e.g. by detection of activation markers by flow cytometry or fluorescence microscopy, by quantitating secreted cytokines via ELISA, quantitation of proliferation ($^3$H thymidine incorporation, CFSE dilution or comparable assays for cellular proliferation), intracellular cytokine staining, cytokine secretion assay, cytokine ELISPOT.

Isolation of said *Aspergillus fumigatus*-specific CD4$^+$ T cells may be performed e.g. by flow-cytometry methods such as FACS® or by magnetic cell separation methods such as MACS®.

The method may comprise the additional step of enrichment of reactive T cells from a sample comprising T cells before adding the at least one in-vivo-target antigen. Enrichment of said reactive T cells may be performed by
  i) fluorescently, or magnetically labeling of one or more activation markers of said reactive T cells, wherein said activation markers are selected from the group consisting of CD154, CD137, cytokines (e.g. IL-2, TNF-alpha, IFN-gamma, IL-17, IL-4, IL-5, IL-13, IL-10, IL-22, IL-9), CD134, CD69, TGF-beta latency associated peptide (LAP), CD121, GARP
  ii) enriching the labeled cells of step i) via flow cytometry or magnetic cell separation methods.

The method may comprise the additional step of expansion of reactive T cells.

Exemplary, enrichment of reactive CD154$^+$ or CD137$^+$ T cells from a sample comprising cells may be performed by using magnetic cell separation technologies such as MACS® (Magnetic-activated cell sorting) or flow cytometric technologies such as FACS® (Fluorescence activated cell sorting) using an antigen-binding fragment such as an antibody against the marker CD154 or any other specific marker accessible on the cell surface.

Exemplary, expansion of said enriched reactive T cells can be performed with methods well known in the art such as culturing them alone or together with irradiated or mitomycin C treated autologous feeder cells and cytokines, such as IL-2. Alternatively specific T cells may be expanded by simply adding the antigens to a mixture of cells comprising the specific T cells. The mixture may also comprise antigen-presenting cells. Cytokines such as IL-2 may be added to enhance T cell proliferation.

In another aspect the present invention provides the use of peptides derived from at least one in-vivo-target antigen of *A. fumigatus*, for loading recombinant MHC class I or class II (HLA) proteins with said peptides to generate functional MHC/peptide complexes or multimeric composites thereof, such as tetramers, pentamers or other higher multimeric structures suitable to bind and/or activate peptide specific T cells,—wherein said at least one in-vivo-target antigen reveals an immune reactivity characterized by
  i) the in vivo existence of antigen-specific T cells comprising more than 60% memory T cells, and
  ii) said antigen-specific T cells further comprise T cells able to produce IFN-gamma upon stimulation at a frequency between 15% and 80% and/or IL17 upon stimulation at a frequency between 5% and 30%.

Said at least one in-vivo-target antigen may be selected from the group consisting of antigens Scw4, Pst1, Shm2, GliT and TpiA or fragments thereof.

Such multimers would also be suitable to label and enrich specific T cells, if the multimers are also labelled, e.g. fluorescently, magnetically or by defined isotopes, similar as described above.

In an aspect the present invention provides a pharmaceutical composition comprising at least one in-vivo-target antigen of *Aspergillus fumigatus* for use as vaccine against aspergillosis, wherein said at least one in-vivo-target antigen reveals an immune reactivity characterized by i) the in vivo existence of antigen-specific T cells comprising more than 60% memory T cells, and ii) said antigen-specific T cells further comprise T cells able to produce IFN-gamma upon stimulation at a frequency between 15% and 80% and/or IL17 upon stimulation at a frequency between 5% and 30%.

Said at least one in-vivo-target antigen is selected from the group consisting of antigens Scw4, Pst1, Shm2, GliT and TpiA or fragments thereof.

In an aspect the present invention provides a pharmaceutical composition comprising *Aspergillus fumigatus*-specific CD4$^+$ T cells for use in immunotherapy of aspergillosis, wherein said *Aspergillus fumigatus*-specific CD4$^+$ T cells are obtained by the present method.

In an aspect the present invention provides a kit for detecting, isolating and/or analyzing *Aspergillus fumigatus*-specific CD4$^+$ T cells comprising a) at least one in-vivo-target antigen, wherein said at least one in-vivo-target antigen reveals an immune reactivity characterized by i) the in vivo existence of antigen-specific T cells comprising more than 60% memory T cells, and ii) said antigen-specific T cells further comprise T cells able to produce IFN-gamma upon stimulation at a frequency between 15% and 80% and/or IL17 upon stimulation at a frequency between 5% and 30%.

b) an antigen-binding fragment specific for one or more activation markers of reactive T cells, wherein said activation markers are selected from the group consisting of CD154, CD137, cytokines (e.g. IL-2, TNF-alpha, IFN-gamma, IL-17, IL-4, IL-5, IL-13, IL-10, IL-22), CD134, CD69, TGF-beta latency associated peptide (LAP), CD121, GARP and wherein said antigen-binding fragment is coupled to a tag.

Said at least one in-vivo-target antigen may be selected from the group consisting of antigens Scw4, Pst1, Shm2, GliT and TpiA or fragments thereof.

The tag may be a magnetic particle or fluorophore.

Definitions

Unless defined otherwise, technical and scientific terms used herein have the same meaning as commonly understood by one of ordinary skill in the art to which this invention belongs.

The term "in-vivo-target antigen" as used herein has a further specific meaning as described herein. Since the method ARTE allows multi-parameter characterization of very rare single *A. fumigatus* protein-specific T cells, the combination of frequencies, naive/memory distribution and effector cytokine production allowed classification of the fungal antigens/proteins into three subgroups: "Immunogenic" antigens/proteins are characterized by high overall T cell frequencies, mainly memory type cells and high IFN-γ and/or IL-17 production. Preferentially, the in-vivo-target antigen reveals an immune reactivity characterized by i) the in vivo existence of antigen-specific T cells containing or comprising more than 60% memory T cells, and ii) said antigen-specific T cells further contain or comprise T cells able to produce IFN-gamma upon stimulation at a frequency between 15% and 80% and/or IL17 upon stimulation at a frequency between 5% and 30%.

In contrast, "exhausting" antigens/proteins were classified due to their low to intermediate overall frequencies, and lack of effector cytokine production, although the majority of cells had a clear memory phenotype. These properties are indicative for an initial in vivo activation leading to acquisition of the memory phenotype but subsequent deletion and/or anergy of specific T cells, potentially due to inappropriate or missing costimulatory signals or alternatively by over-activation due to chronic presence of the antigen. These two subgroups with obvious immune reactivity in vivo contrast with the third group, which we termed "non-target" antigens/proteins, since they induce high overall T cell frequencies, but strikingly a large proportion of the cells is still in the naive state and also lacks effector cytokine production. This indicates that no immune reactivity is induced in vivo.

The amino acid sequences of Scw4, Pst1, Shm2, GliT and TpiA are given in SEQ ID NO:1, SEQ ID NO:2, SEQ ID NO:3, SEQ ID NO:4 and SEQ ID NO:5, respectively (in the one-letter code of amino acids). The gene/protein names ShmB or SHMT may also be used for Shm2. The gene/protein name Tpi1 may also be used for TpiA. The term "in-vivo-target antigen" Scw4, Pst1, Shm2, GliT and TpiA as used herein refers to all constellations of the respective antigen which retains the intended function of being an in-vivo-target antigen of *Aspergillus fumigatus* as defined herein. In other words, the divergences to the SEQ ID Nos:1, SEQ ID NO:2, SEQ ID NO:3, SEQ ID NO:4 and SEQ ID NO:5, respectively, should not affect their immunogenic potential as in-vivo-target antigen, respectively, of *Aspergillus fumigatus* as disclosed herein. Therefore, the in-vivo-target antigens Scw4, Pst1, Shm2, GliT and TpiA, respectively, can be the full length protein of SEQ ID NO:1, SEQ ID NO:2, SEQ ID NO:3, SEQ ID NO:4 and SEQ ID NO:5, respectively. It can also be a variant thereof which have some amino acids deleted, added or replaced while still retaining the function of being an in-vivo-antigen target of *Aspergillus fumigatus*. Therefore, included in this definition are variants of the amino acid sequences in SEQ ID NO: 1, SEQ ID NO:2, SEQ ID NO:3, SEQ ID NO:4 and SEQ ID NO:5, respectively, such as amino acid sequences essentially similar to SEQ ID NO: 1, SEQ ID NO:2, SEQ ID NO:3, SEQ ID NO:4 and SEQ ID NO:5, respectively, having a sequence identity of at least 70%, or at least 75%, 80%, 85%, 90%, 95%, 97%, 98% or 99% at the amino acid sequence level. In the context of the present invention, "sequence identity" may be determined using pairwise alignments using alignments programs for amino acid sequences well known to the art.

The in-vivo-target antigen of Scw4, Pst1, Shm2, GliT and TpiA, respectively, can also be a fragment of the protein Scw4, Pst1, Shm2, GliT and TpiA, respectively, e.g. a minimal peptide of 6-15 amino acids in length. Preferentially, the in-vivo-target antigen Scw4, Pst1, Shm2, GliT and TpiA, respectively, is a peptide pool. The peptide pool may comprise several peptides covering the complete or part of the sequences of Scw4, Pst1, Shm2, GliT and TpiA, respectively, peptides with may or may have not overlapping amino acid sequences. More preferentially, the in-vivo-peptide antigen is a peptide pool comprising 15meric overlapping peptides (e.g. 11 amino acids overlap) and spanning the whole protein sequence.

In general all amino acid variations are included under this definition, which do not lead to intentional changes in the recognition or activation of the specific T cells which are recognizing the corresponding peptide or protein with the original peptides sequence as defined in the present application.

The term specific T cells as used herein refers to a T cell expressing a certain T cell antigen receptor with the capacity to recognize only a specific peptide bound to a certain MHC molecule but not to the same MHC molecule complexed with other irrelevant peptides. "Specific" does not exclude that several possible peptides may exist which can bind to the MHC molecule and which are then recognized by the same TCR. This can be peptides with high homology, i.e. similar amino acid sequences, but even complete unrelated peptides may have this capacity. Specificity does rather mean that a TCR does only react to small selection of peptide/MHC complexes out of large reservoire of possible combinations, and in this way the particular T cell is specific for the antigen, the peptide is derived of but it may not exclude the possibility that cross-reactivity against other peptide derived from similar or unrelated antigen occur. That a certain TCR recognized a certain MHC/peptide combination can be tested with various technologies. Direct binding of the TCR can be demonstrated by using multimeric complexes (tetramers, pentamers) of the specific MHC/peptide (antigen) complex labelled with a fluorochrome. Such multimeric MHC molecules are well known in the art. Briefly they consist of the extracellular protein domain of MHC class I or class II (in humans HLA class I or class II, Human Leukocyte Antigen) consisting of two protein chains, which may be linked via an peptide linker. Into the antigen binding "groove" of the MHC molecule antigenic peptides (e.g. 9-15mers), e.g. derived from the proteins identified in present invention, can be loaded. In this way a functional MHC/peptide monomer is generated which can bind to the specific TCR recognizing the combination of MHC+peptide. Typically this binding affinity is low. Therefore multimeric structures are generated via various technologies known in the art to fuse several MHC/peptide complexes (e.g. 4, 5, 6 or more) to generate a high avidity protein which can bind simultaneously to multiple TCRs on the T cell surface and generate stable interaction. Binding of such multimeric complexes may also induce specific T cell activation.

Alternatively recognition can be demonstrated by measuring the response of the T cells to activation by the specific peptide/MHC molecule, e.g. by adding the peptide to a mixture of autologous antigen presenting cells and the T cells for several hours or days and measuring cytokine expression, expression of surface markers such as CD154 or CD137 or proliferation of the T cells.

The term "antigen-reactive" T cell is used herein mostly overlapping with the term "antigen-specific" since T cells which can specifically recognize a specific peptide/MHC combination as described above become activated by this stimulus via their TCR, i.e. they express certain cytokines, activation markers or start to proliferate. This sign of activation can then be used to identify the cells as described above. "Antigen-reactive" refers to T cells which are activated via there TCR but not to T cells which are activated independently of the TCR, e.g. via cytokines produced by other activated cells in the culture. This type of "bystander" activation is not a cell intrinsic property but depends on the presence of other cells, whereas specific activation strictly depends on the presence of the specific peptide/MHC complex (see definition of a specific peptide above) and potentially co-stimulatory molecules, which do not induce activation on their own.

The groups of antigen-specific and antigen-reactive T cells do large overlap, however anergic or inactivated T cells may exist which still have the specific TCR but lost their potential to become activated, i.e. they are excluded from the group of antigen-reactive T cells.

Antigen-specificity and reactivity can be determined in all types of T cells. In particular conventional (Tcon) and regulatory T cells (Treg) can be distinguished. Treg are defined here as Foxp3$^+$ CD4$^+$ T cells which typically do also express CD25 and lack expression of CD127. They represent a separate T cell lineage required to maintain tolerance against auto-antigens and harmless foreign antigens. Tcon cells as defined here comprise all T cells which are not Treg. In both populations Tcon and Treg naive (no previous contact to antigen) and antigen-experienced or memory T cells (Tmem) can be found, which substantially differ in many phenotypical and functional aspects. Each T cell have a specific antigen receptor (T cell receptor, TCR) for one particular antigen. Therefore T cells with specificity for a particular antigen are typically rare, i.e. about 1 in 1 million for naive T cells and typically <1% for memory T cells, except in certain acute infectious diseases. Therefore it requires analysis methods able to identify these rare cells to study the immune status of a certain patient against a defined antigen or pathogen.

The term "antigen-binding fragment" as used herein refers to any moiety that binds preferentially to the desired target molecule of the cell, i.e. the antigen. The term moiety comprises, e.g., an antibody or antibody fragment. The term "antibody" as used herein refers to polyclonal or monoclonal antibodies which can be generated by methods well known to the person skilled in the art. The antibody may be of any species, e.g. murine, rat, sheep, human. For therapeutic purposes, if non-human antigen binding fragments are to be used, these can be humanized by any method known in the art. The antibodies may also be modified antibodies (e.g. oligomers, reduced, oxidized and labelled antibodies). The term "antibody" comprises both intact molecules and antibody fragments, such as Fab, Fab', F(ab')2, Fv and single-chain antibodies. Additionally, the term "antigen-binding fragment" includes any moiety other than antibodies or antibody fragments that binds preferentially to the desired target molecule of the cell. Suitable moieties include, without limitation, oligonucleotides known as aptamers that bind to desired target molecules The term "tag" as used herein refers to the coupling of the antigen-binding fragment, e.g. an antibody or fragment thereof, to other molecules, e.g. particles, fluorophores, haptens like biotin, or larger surfaces such as culture dishes and microtiter plates. In some cases the coupling results in direct immobilization of the antigen-binding fragment, e.g. if the antigen-binding fragment is coupled to a larger surface of a culture dish. In other cases this coupling results in indirect immobilization, e.g. an antigen-binding fragment coupled directly or indirectly (via e.g. biotin) to a magnetic bead is immobilized if said bead is retained in a magnetic field. In further cases the coupling of the antigen-binding fragment to other molecules results not in a direct or indirect immobilization but allows for enrichment, separation, isolation, and detection of cells according to the present invention, e.g. if the antigen-binding fragment is coupled to a fluorophore which then allows discrimination of stronger labeled cells, weaker labeled cells, and non-labeled cells, e.g. via flow cytometry methods, like FACSorting, or fluorescence microscopy.

The term "particle" as used herein refers to a solid phase such as colloidal particles, microspheres, nanoparticles, or beads. Methods for generation of such particles are well known in the field of the art. The particles may be magnetic particles. The particles may be in a solution or suspension or they may be in a lyophilized state prior to use in the present invention. The lyophilized particle is then reconstituted in convenient buffer before contacting the sample to be processed regarding the present invention.

The term "magnetic" in "magnetic particle" as used herein refers to all subtypes of magnetic particles which can be prepared with methods well known to the skilled person in the art, especially ferromagnetic particles, superparamagnetic particles and paramagnetic particles. "Ferromagnetic" materials are strongly susceptible to magnetic fields and are capable of retaining magnetic properties when the field is removed. "Paramagnetic" materials have only a weak magnetic susceptibility and when the field is removed quickly lose their weak magnetism. "Superparamagnetic" materials are highly magnetically susceptible, i.e. they become strongly magnetic when placed in a magnetic field, but, like paramagnetic materials, rapidly lose their magnetism.

The term "activation marker" as used herein refers to proteins specifically expressed on the cell surface of T cells following their activation via their specific antigen-receptor, usually within 1-48 hours after activation. Activated T cells may comprise CD4 T cells, CD8 T cells, naïve T cells, memory T cells, gamma-delta T cells or regulatory T-cells. Such activation markers are, for example, CD154, CD137, secreted or membrane-anchored cytokines, e.g. IL-4, IL-5, IL-13, IFN-gamma, IL-10, IL-2, IL-22, TNF-alpha or "latent TGF-beta" (LAP), GARP (LRRC32), CD121a/b.

CD154 is a member of the TNF gene family and, inter alia, is expressed by various cells, particularly by T lymphocytes. CD154 is rapidly (within minutes) downregulated by the stimulated T lymphocytes upon contact with its receptor CD40. CD154 can be used to detect T lymphocytes independently of their functional potential. The use of CD154 in the detection and separation of T lymphocytes leads to reliable detection and isolation of T lymphocytes, possible independently of their function, i.e. all antigen-specific T lymphocytes in a sample can be determined and separated.

A method is disclosed in WO2004/027428 for the detection and/or isolation of antigen-specific T lymphocytes in a suspension following activation with an antigen, in which method the suspension is contacted with a CD40/CD154 system inhibitor, intra- and/or extracellular determination of CD154 is effected, and the cells having CD154 are detected and/or isolated.

Addition of a CD40/CD154 system inhibitor impairs or inhibits the interaction and signalling between CD40 and CD154. CD40/CD154 system inhibitors can be any of molecules or even physical exposures capable of blocking or inhibiting the interaction between CD40 and CD154. Accordingly, the inhibiting agent can be an antibody, e.g. one directed against CD40, a molecule, a caesium or lithium ion having an effect on the interaction between CD40 and CD154. Of course, said agent can also be a substance inhibiting the secretion or endocytosis in the cell, such as brefeldin A (Bref-A). Bref-A inhibits the Golgi apparatus and the secretion of a variety of cytokines. These substances ensure that CD40, CD154, the interaction between the two of them, or the CD40/CD154 system are modified in such a way that CD154 either is no longer down-regulated and/or degraded on the cell surface, or, provided it is still within the cell, no longer transported therein. Such interruption of the transport within the cell prevents degradation of CD154. Consequently, CD154 is stabilized inside or outside the cell as an external receptor, thereby allowing detection and subsequent isolation using detection methods well-known to those skilled in the art.

EP2306191B1 disclosed that the use of CD154 as a negative selection marker greatly increases the window of time for the use of the marker CD137 for the positive selection of regulatory T cells (Treg) and that 2 to 24 hours after activation, regulatory T-cells can be isolated with great purity and yield. Therefore it is possible with the present invention to analyse rare antigen-specific Treg cells, i.e. *Aspergillus fumigatus*-specific CD4+ T cells, using the combination of activation markers CD137 and CD154.

For isolation (selection or enrichment) in principle any sorting technology can be used. This includes for example affinity chromatography or any other antibody-dependent separation technique known in the art, which allows processing. Any ligand-dependent separation technique known in the art may be used in conjunction with both positive and negative separation techniques that rely on the physical properties of the cells.

An especially potent parallel sorting technology is magnetic cell sorting. The term "magnetic cell sorting" or "magnetic cell sorting process" is used herein to refer to procedures for cell separation (cell sorting) including, but are not limited to, magnetic separation using antibodies linked to colloidal magnetic particles or micron-sized magnetic particles (e.g. 1-10 μm).

Methods to separate cells magnetically are commercially available e.g. from Invitrogen, Stem cell Technologies, in Cellpro, Seattle or Advanced Magnetics, Boston. For example, autologous monoclonal antibodies can be directly coupled to magnetic polystyrene particles like DYNAL® M 450 (superparamagnetic beads) or similar magnetic particles and used e.g. for cell separation. Alternatively, antibodies can be biotinylated or conjugated with digoxigenin and used in conjunction with avidin or anti-digoxigenin coated affinity columns. In a preferred embodiment however, monoclonal antibodies are used in conjunction with colloidal superparamagnetic microparticles having an organic coating by e.g. polysaccharides (Miltenyi et al., 1990, Cytometry 11:231-8). These particles can be used having a size of 10 to 200 nm, preferably between 40 and 100 nm, and can be either directly conjugated to autologous antibodies or used in combination with anti-immunoglobulin, avidin or anti-hapten-specific microbeads. Polysaccharide-coated superparamagnetic particles are commercially available from Miltenyi Biotec GmbH, Germany.

The cells can be analyzed (characterized) after selective activation with one or more of the in-vivo-target antigens of *Aspergillus fumigatus* as disclosed herein according to all methods known to the person skilled in the art. Preferred for the characterization of cells are in particular cell sorting (e.g. further magnetic cell sorting (MACS)), fluorescence activated cell sorting (FACS), ELISA, PCR and/or all fluorescence microscopes known in the art.

The sample comprising T cells can be any sample comprising T cells. E.g. the sample is directly derived from blood, peripheral mononuclear blood cells (PBMC), body tissue or cells from tissue fluids of animals, preferentially mammals such as humans, mouse, rat, sheep or dogs. The sample comprising T cells may also be a sample in which T cells are enriched from e.g. a blood sample. The T cells may be the only subtype of cells in the sample, or in addition to the T cells may be present antigen presenting cells, or further cells of the blood. The sample comprising T cells may encompass expanded T cells or non-expanded T cells.

The separated *Aspergillus fumigatus*-specific CD4+ T cells can be used before and/or after cloning and/or growing and/or concentrated in cell mixtures as pharmaceutical composition in the immunotherapy of aspergillosis. It is additionally possible for the coding gene sequences of the TCR (T-cell receptor) to be isolated from the separated *Aspergillus fumigatus*-specific CD4+ T cells and be used for further therapeutic purposes such as, for example, for cellular therapies. It is additionally possible to employ the *Aspergillus fumigatus*-specific CD4+ T cells in the form mentioned in further investigations and/or analyses. The pharmaceutical composition can be used for the treatment and/or prevention of diseases in mammals, possibly including administration of a pharmaceutically effective amount of the pharmaceutical composition to the mammal.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

Embodiments

In one embodiment of the invention a human sample, e.g. blood or tissue from a patient suffering from IA or at risk for an *A. fumigatus* infection is obtained. Patients at risk for fungal infections are immunocompromised patients, e.g. following chemotherapy, hematopoetic stem cell transplantation, HIV patients, or patients with intrinsic genetic defects leading to immune deficiency. One or more in-vivo-target antigens of *Aspergillus fumigatus*, wherein said at least one in-vivo-target antigen reveals an immune reactivity characterized by i) the in vivo existence of antigen-specific T cells comprising more than 60% memory T cells, and ii) said antigen-specific T cells further comprise T cells able to produce IFN-gamma upon stimulation at a frequency between 15% and 80% and/or IL17 upon stimulation at a frequency between 5% and 30%, and wherein said at least one in-vivo-target antigen may be selected from the group consisting of antigens Scw4, Pst1, Shm2, GliT and TpiA is added to the sample. After incubation of 6-18 hours, the *Aspergillus fumigatus*-specific CD4+ T cells are detected via expression of activation markers such as CD154, CD137, cytokines or proliferation and quantitated and/or characterized, e.g. by flow-cytometry or purified via FACS sorting. Alternatively, the *Aspergillus fumigatus*-specific CD4+ T cells are isolated by labeling the cells of the sample with an antibody against the marker molecules mentioned above coupled to a magnetic bead and separated magnetically by applying a magnetic field.

Alternatively, the *Aspergillus fumigatus*-specific CD4+ T cells are directly labelled with an MHC multimer loaded with one or several peptides derived from the in vivo target antigens identified in the present invention and the labelled cells are similarly characterized or isolated as described above by well known methods in the art. The information about the frequency, phenotype and functional properties of the *A. fumigatus* specific cells identified as described above may be used to diagnose invasive fungal infection or to identify sensitization of the patient's immune system against the fungus.

In a similar way other *A. fumigatus* related diseases may be diagnosed or analysed via characterization of the *A. fumigatus* specific T cells from the patients. Such diseases include cystic fibrosis, allergies, asthma, chronic obstructive pulmonary disease (COPD). In these patients overshooting or chronic immune activation against the fungus contributes to the disease phenotype but is often difficult to be specifically determined. Analysing the specific T cell response against the in vivo target proteins can be used to identify the type of immune response and help to select the appropriate therapeutic concept. Increased frequencies identify invasive aspergillosis. Alterations in the Treg/effector T cell ratio may identify not properly regulated immune reactions, e.g. allergies or chronic activation, certain cytokine patterns identify patient subgroups: allergic or asthmatic patients have increased Th2 cytokines alone or together with Th17 cytokines, patients with strong neutrophil contribution to the inflammation in the lung have increased Th17 cytokines, or patients with a defect in the immune response (no/low effector cytokine production), e.g. T cell exhaustion as a result of in vivo overstimulation.

In one embodiment of the invention T cells specific for one or more in-vivo-target antigens of *Aspergillus fumigatus*, wherein said at least one in-vivo-target antigen reveals an immune reactivity characterized by i) the in vivo existence of antigen-specific T cells comprising more than 60% memory T cells, and ii) said antigen-specific T cells further comprise T cells able to produce IFN-gamma upon stimulation at a frequency between 15% and 80% and/or IL17 upon stimulation at a frequency between 5% and 30%, and wherein said at least one in-vivo-target antigen may be selected from the group consisting of antigens Scw4, Pst1, Shm2, GliT and TpiA, are isolated as described above, e.g. using CD154 as a marker for activated effector T cells. The cell can be isolated from the patient or from the donor in case of bone marrow transplantation or be isolated from a third party donor with related MHC molecules. The isolated T cells can then be directly infused into a patient with an *A. fumigatus* infection, e.g. invasive fungal infection. Alternatively the T cells can be expanded in vitro and infused into the patient with the aim to enhance the immune defense against the fungal infection and cure the patient.

The antigens can also be used to isolate and expand *A. fumigatus* specific Foxp3+ regulatory T cells (Treg), e.g. by sorting specifically CD137 expressing T cells or CD154-CD137+ T cells after a short 6-12 hours stimulation with the antigen in vitro. These Treg can similarly be expanded in vitro or be directly used for infusion into patients, e.g. with chronic inflammatory reactions or allergies against *A. fumigatus*.

In one embodiment of the invention one or several in-vivo-target antigens of *Aspergillus fumigatus*, which reveal an immune reactivity characterized by i) the in vivo existence of antigen-specific T cells comprising more than 60% memory T cells, and ii) said antigen-specific T cells further comprise T cells able to produce IFN-gamma upon stimulation at a frequency between 15% and 80% and/or IL17 upon stimulation at a frequency between 5% and 30%, and which may be selected from the group consisting of antigens Scw4, Pst1, Shm2, GliT and TpiA are used to vaccinate people at risk for getting *A. fumigatus* infections or allergies or chronic inflammatory reactions.

The components necessary to perform the methods disclosed herein may be provided as a kit. Each kit contains the components necessary to perform selective activation of *Aspergillus fumigatus* specific CD4+ T cells in a sample comprising T cells and detection, isolation and/or analysis of said *Aspergillus fumigatus*-specific CD4+ T cells. A kit for detecting, isolating and/or analyzing *Aspergillus fumigatus*-specific car T cells comprises a) at least one in-vivo-target-antigen, wherein said at least one in-vivo-target antigen reveals an immune reactivity characterized by i) the in vivo existence of antigen-specific T cells comprising more than 60% memory T cells, and ii) said antigen-specific T cells further comprise T cells able to produce IFN-gamma upon stimulation at a frequency between 15% and 80% and/or IL17 upon stimulation at a frequency between 5% and 30%, and wherein said at least one in-vivo-target antigen may be selected from the group consisting of antigens Scw4, Pst1, Shm2, GUT and TpiA, b) Antigen-binding fragment specific for one or more activation markers of reactive T cells, wherein said activation markers are selected from the group consisting of CD154, CD137, cytokines (e.g. IL-2, IL-4, IL-5, IL-9, IL-13, IL-17, IL-22, IFN-gamma, TNF-alpha), CD134, CD69, TGF-beta latency associated peptide (LAP), and wherein said antigen-binding fragment is coupled to a tag.

Preferentially, the tag is a magnetic particle such as a magnetic bead or a fluorophore.

For use in magnetic cell sorting the antigen binding fragments are coupled to magnetic particles as described herein. The magnetic particles, e.g. MicroBeads (Miltenyi Biotec GmbH), of the kit may be in a solution or suspension or they may be in a lyophilized state prior to use in a method of the present invention. The lyophilized particle is then reconstituted in convenient buffer before contacting with the sample containing neuronal cells to be processed regarding the present invention.

EXAMPLES

Example 1

Materials and Methods

Blood Donors

Buffy coats from healthy donors were obtained from the Institute for Transfusion Medicine, University Hospital Dortmund after informed consent. Peripheral blood mononuclear cells (PBMCs) were isolated by FICOLL®-Paque (media comprising neutral, highly branched, high mass, hydrophilic polysaccharide) (GE Healthcare Life Sciences, Freiburg, Germany) density gradient centrifugation.

Preparation of *A. fumigatus* Lysates

For the generation of all *A. fumigatus* (ATCC46645) protein extracts, except for the lysate of resting conidia (RC), 2×10E8 conidia were inoculated in 200 ml YPD medium and cultured at 37° C. and 200 rpm. Swollen conidia (SC) were harvested after 6 h, germinated conidia (GC) after 8 h, and mycelium after 20 h of cultivation. Cells were recovered by centrifugation (RC, SC, GC) or filtration (mycelium) and washed with water before storage at −80° C. Total RC, SC, or GC lysates were generated by disruption of frozen cells in saline[0.9% (w/v) NaCl] using a Micro-Dismembrator (Sartorius). For total mycelial lysate, frozen mycelium was ground in liquid nitrogen by using a mortar and pestle and resuspendend in PBS supplemented with 2 mM $MgCl_2$. Total soluble protein fractions of the lysates (crude lysates) were obtained after removal of insoluble material (cell wall pellet) by centrifugation for 15 min at 10,000×g. Fractionated mycelial protein extracts were obtained by sequential centrifugation of total mycelial lysate. The cell wall protein fraction was processed by resuspension of the cell wall pellet (15 min of centrifugation at 10000×g) in PBS/2 mM $MgCl_2$. By centrifugation of the crude mycelial lysate at 100,000×g for 60 min, the cell membrane-enriched protein fraction (pellet) was separated from the cytosolic protein fraction. Cell membrane extract was generated by resuspension of the membrane pellet in PBS/2 mM $MgCl_2$.

Generation of Recombinant *A. fumigatus* Proteins

The recombinant proteins used were generated by standard technologies known in the field, i.e. cloning of the coding sequences into a suitable expression vector adding a suitable tag for subsequent protein purification (e.g. 6 his tag or MBP-HIS-tagged). The proteins were expressed in *E. coli*, namely Crf2, GliT, Scw4, Aspf3, Shm2, CpcB, Aspf22, Pst1 and TpiA or in *Pichia pastoris* FG-GAP repeat protein, [devoid of the sequence encoding the 25 amino acids N-terminal secretion signal peptide (Δ25FG-GAP)] and of AspF2. All peptide sequences relevant to the present invention are listed below as shown in SEQ ID NO:1, SEQ ID NO:2, SEQ ID NO:3, SEQ ID NO:4 and SEQ ID NO:5. All proteins were purified by affinity chromatography using an Äkta explorer purification system (GE Healthcare). If necessary, an ion exchange column (SOURCE 15Q, GE Healthcare) was used for further purification. Generally, all buffer exchanges were conducted using HIPREP® 26/10 desalting columns (column packed with crosslinked dextran G-25 Fine) (GE Healthcare). All HIS-tagged proteins were applied to a Ni SEPHAROSE® (crosslinked agarose) 6 Fast Flow (GE Healthcare) column, and eluted with 250 mM imidazole. MPP-tagged proteins were loaded onto an Amylose Resin HF (New England Biolabs) column and eluted with 10 mM maltose. The MBP-HIS-tag of MBP-tagged proteins and the HIS-tag of AspF3 were cleaved using TEV-protease and removed by its binding to Ni SEPHAROSE® (crosslinked agarose). After buffer exchange to 20 mM Tris-HCl pH 8 (CpcB, Pst1, TpiA) or 20 mM Tris-HCl pH 8.5, 6 M urea (Scw4), corresponding proteins were further purified by ion exchange chromatography using an NaCl gradient for elution. Scw4 was further purified by reversed phase chromatography (Source 15RPC, GE Healthcare) after exchanging the buffer to 0.05% (v/v) trifluoroacetic acid, 10% (v/v) acetonitril. Purified Scw4 was lyophilized and resolved in PBS. For all other purified proteins, the buffer was exchanged to PBS (FG-GAP, Pst1, AspF22, AspF2, GliT) or 0.9% NaCl (Shm2, CpcB, AspF3, TpiA).

Stimulation of Antigen-reactive T Cells

PBMCs were resuspended at a concentration of 1×10E7/ml in RPMI-1640 (Miltenyi Biotec, Bergisch Gladbach, Germany), supplemented with 5% (v/v) human AB-serum (BioWhittaker/Lonza, Walkersville, Md., USA), and 2 mM L-glutamine (PAA Laboratories, Pasching, Austria). Cells were stimulated for 7 hours with the following antigens: *A. fumigatus* lysates (each 40 μg/ml), *C. albicans*-lysate (20 μg/ml; Greer Laboratories, Lenoir, N.C., USA), CMV-lysate (10 μg/ml, Siemens Healthcare Diagnostics, Marburg, Germany), recombinant *A. fumigatus* proteins (Crf2, Pst1, Aspf2, Aspf3, Shm2, FG-GAP, GliT, Aspf22, CpcB, TpiA, Scw4; each 20 μg/ml) or peptide pools (*C. albicans* MP65, Gel1, Crf1, Aspf3, CatB, Sod3, Shm2; each 0.6 nmol/peptide/ml; all from Miltenyi Biotec), or pools of proteins according to the classification into immunogenic (Scw4, CRF1, CRF2, Pst1, Shm2, each 20 μg/ml), non-target (Gel1, CatB; each 20 μg/ml) and exhausted (Aspf2, CpcB, Aspf3, FG-GAP; each 20 μg/ml). 1 μg/mlCD40 and 1 μg/ml CD28 functional grade pure antibody (both Miltenyi Biotec) was added. In some experiments, $CD45RA^+$ cells were depleted from PBMCs prior stimulation using CD45RA microbeads and LD columns (Miltenyi Biotec).

Enrichment and Characterization of Antigen-reactive T Cells

Enrichment of reactive CD154+ T cells or combined enrichment of CD154+/CD137+ T cells was performed using the CD154 MicroBead Kit alone, or in combination with the CD137 MicroBead Kit (both Miltenyi Biotec). In brief, cells were indirectly magnetically labeled with CD154-Biotin and CD137-PE followed by anti-Biotin Microbeads and anti-PE Microbeads and enriched by two sequential MS MACS columns (Miltenyi Biotec). For analysis of cytokine expression, 1 µg/ml Brefeldin A (Sigma Aldrich) was added for the last 2 hours of stimulation. Surface staining was performed on the first column, followed by fixation, permeabilization (Inside stain Kit; Miltenyi Biotec) and intracellular cytokine staining on the second column, as described (Bacher et al J Immunol 2013), or staining of Foxp3 using the Foxp3 Staining Buffer Set (Miltenyi Biotec).

In Vitro Expansion and Re-stimulation of Antigen-reactive T Cell Lines

Magnetically enriched CD154+ T cells were expanded with 1:100 mitomycin C (Sigma Aldrich) treated autologous feeder cells in X-Vivo™15 (BioWhittaker/Lonza), supplemented with 5% (v/v) AB-serum (BioWhittaker/Lonza), 200 U/ml IL-2 (PROLEUKIN® (aldesleukin); Novartis, Nürnberg, Germany) and 100 U/ml penicillin, 100 µg/ml streptomycin, 0.25 µg/ml amphotericin B (Antibiotic Antimycotic Solution, Sigma Aldrich) at a density of 2.5×10E6 cells/cm². During expansion for 2-3 weeks, medium was replenished and cells were split as needed.

5×10E5 expanded T cells were re-stimulated with autologous CD3-depleted (CD3 MicroBeads; Miltenyi Biotec) PBMC in a ratio of 1:1 in 96-well flat bottom plates with different antigens in presence of 1 µg/ml CD28 functional grade pure Ab for 2 h plus additional 4 h with 1 µg/ml Brefeldin A (Sigma Aldrich). After fixation and permeabilization cells were stained intracellularly for CD154 and cytokines.

Flow Cytometry

Different combinations of the following monoclonal antibodies were used according to manufacturer's recommendations: CD4-VioBlue, CD4-FITC, CD4-APC-Vio770 (VIT4), CD3-APC (BW264/56), CD14-VioGreen, CD14-PerCP (TÜK4), CD20-VioGreen, CD20-PerCP (LT20), CD8-VioGreen (BW135/80), CD45RO-FITC, CD45RO-PerCP (UCHL-1), CCR7-PE (REA108), CD45RA-APC, CD45RA-FITC (T6D11), anti-Biotin-PE, anti-Biotin-VioBlue (Bio3-18E7), CD154-PE, CD154-APC, CD154-VioBlue (5C8), TNF-α-FITC, TNF-α-PE-Vio770 (cA2), IFN-γ-FITC, IFN-γ-APC, IFN-γ-PE (45-15), IL-2-APC (N7.48A), IL-17-FITC, IL-17-PE (CZ8-23G1), IL-10-PE (B-T10), IL-4-PE (7A3-3), CD137-PE (4B4-1) (all Miltenyi Biotec), CD45RO-PE.Cy7 (UCHL-1, BD Bioscience, San Jose, Calif., USA), IFNγ-PerCP-Cy5.5 (4S.B3; BioLegend, San Diego, Calif., USA), IL-22-PE (142928; R&D Systems Europe, Ltd., Abingdon, UK), Foxp3-PerCP-Cy5.5 (PCH101; eBioscience, San Diego, Calif., USA). Data were acquired on a MACSQuant® analyzer and MACSQuantify™ software was used for analysis (both Miltenyi Biotec).

Statistical Analysis

Statistical tests were performed with GraphPad PRISM® software 5.0 (GraphPad Software, La Jolla, Calif., USA) using two-tailed paired Student's t-test. P values of <0.05 were considered statistically significant.

Example 2

Human CD4+ T cell response against lysates of different *A. fumigatus* morphotypes CD4+ T cells specifically reacting against *A. fumigatus* can be identified using CD154 expression as a specific read-out for antigen activated CD4+ T cells after short in vitro stimulation with fungal lysate (Bacher et al, J Immunol 2013; Frentsch et al, Nat Med 2005) To analyze against which *A. fumigatus* morphotype the human T cell response is directed, peripheral blood mononuclear cells (PBMC) from healthy donors were stimulated for 7 hours with crude lysates from resting, swollen and germinating conidia or mycelia, containing the total soluble fraction of the mechanically disrupted fungal cells. Reactive CD154-expressing CD4+ T cells were identified by flow-cytometry. Although all lysates induced a small population of CD154 expressing CD4+ T cells, the frequency of reactive cells stimulated with resting conidia lysate was significantly lower, compared to stimulation with lysates from other morphotypes (FIG. 1A, B). To enable the direct ex vivo phenotypic and functional characterization of the specific T cells, we next magnetically pre-enriched the rare antigen-reactive CD154+ T cells from larger cell numbers (1×10E7 PBMC). Again, a significantly higher number of target cells could be detected after stimulation with lysates of the more progressed development stages versus the resting conidia lysate (FIG. 1C). However, analysis of cytokine production and phenotype revealed no major differences of T cells stimulated with the different *A. fumigatus* morphotype lysates: as shown in FIG. 1D, against all lysates a high frequency of TNF-α, and IL-2 producers could be detected, whereas the production of the lineage defining cytokines IFN-γ and IL-17 was only low, although IFN-γ production was clearly predominant over IL-17, as already described before (Bacher et al J Immunol 2013, Schonbrunn et al J Immunol 2012). Similarly, irrespective of the *A. fumigatus* lysate used for stimulation a comparable amount of reactive memory T cells was detected (FIG. 1E).

In summary, these results demonstrate that reactive memory CD4+ T cells against different morphotypes of *A. fumigatus* are present in healthy human donors and suggest that the strongest T cell response is directed against the actively growing fungus.

Examples 3

Swollen and Germinating Conidia as Well as Mycelia Contain Overlapping T Cell Antigens We next addressed the question, whether the reactive CD4+ T cells recognize different or the same antigens expressed by the various *A. fumigatus* morphotypes. To this end, specific T cell lines were generated by expanding the magnetically enriched CD154+ T cells after stimulation with the different morphotype lysates. Upon re-stimulation the T cell lines initially stimulated with protein extracts of swollen conidia, germinating conidia and mycelia were equally reactive to either lysate, as shown by re-expression of CD154 and production of cytokines (FIG. 2A, B). However, the re-stimulation with resting conidia lysate was in each case significantly lower, suggesting that a considerable proportion of T cell antigens, which are present in the metabolically active morphotypes (swollen and germinating conidia, mycelia), are missing in the resting conidia lysate. Furthermore, resting conidia-reactive T cell lines reacted equally well to re-stimulation with each lysate, suggesting that resting conidia do not contain a significant fraction of T cell target proteins solely present in the dormant stage. As expected, none of the expanded cell lines reacted upon re-stimulation with CMV-lysate as a control antigen, providing evidence for the specificity of the expanded fungus-reactive T cell lines. As for the ex vivo response, we

Example 4

ARTE allows direct characterization of human CD4+ T cells reacting against single A. fumigatus proteins So far, only few single proteins of A. fumigatus have been analyzed and directly compared in their capacity to elicit CD4+ T cell responses in humans. In particular the direct qualitative and quantitative characterization of the responding T cells is missing, which avoids an experimental bias due to prolonged in vitro culture. However, the quality of the T cell response generated in vivo may provide important insight into the immunogenic properties of specific antigenic proteins.

Therefore we performed multi-parameter analysis of the T cells specific for a panel of 15 selected A. fumigatus proteins with different biological functions and cellular localization. Either recombinant proteins or synthesized 15mer peptide pools covering the complete protein sequence were used for stimulation. The analyzed proteins included cell wall, GPI-anchored, secreted, as well as cytosolic proteins and were chosen based on their high abundance within the conidial, mycelia or secreted proteome and/or their previous description as being immunogenic, based on T cell or serum reactivity. A concentration of 20 µg/ml of recombinant proteins for the stimulation of 1×10E7 PBMCs was determined based on titration of the single proteins on expanded total mycelia-reactive T cell lines (data not shown). The C. albicans protein MP65 had previously been described as a major antigen target of human T cell responses and served as a positive control.

Against the majority of the analyzed single A. fumigatus proteins no reactive CD4+ T cells above background could be detected by standard flow-cytometry without pre-enrichment (data not shown). To enable the direct ex vivo detection of reactive CD4+ T cells against the single A. fumigatus proteins, we performed ARTE from 1×10E7 stimulated PBMCs. Although the frequencies upon single protein stimulation were significantly lower as upon stimulation with A. fumigatus or C. albicans crude lysates, specific T cells against single proteins could be clearly detected compared to the non-stimulated control (FIG. 3A).

Figure 3A:
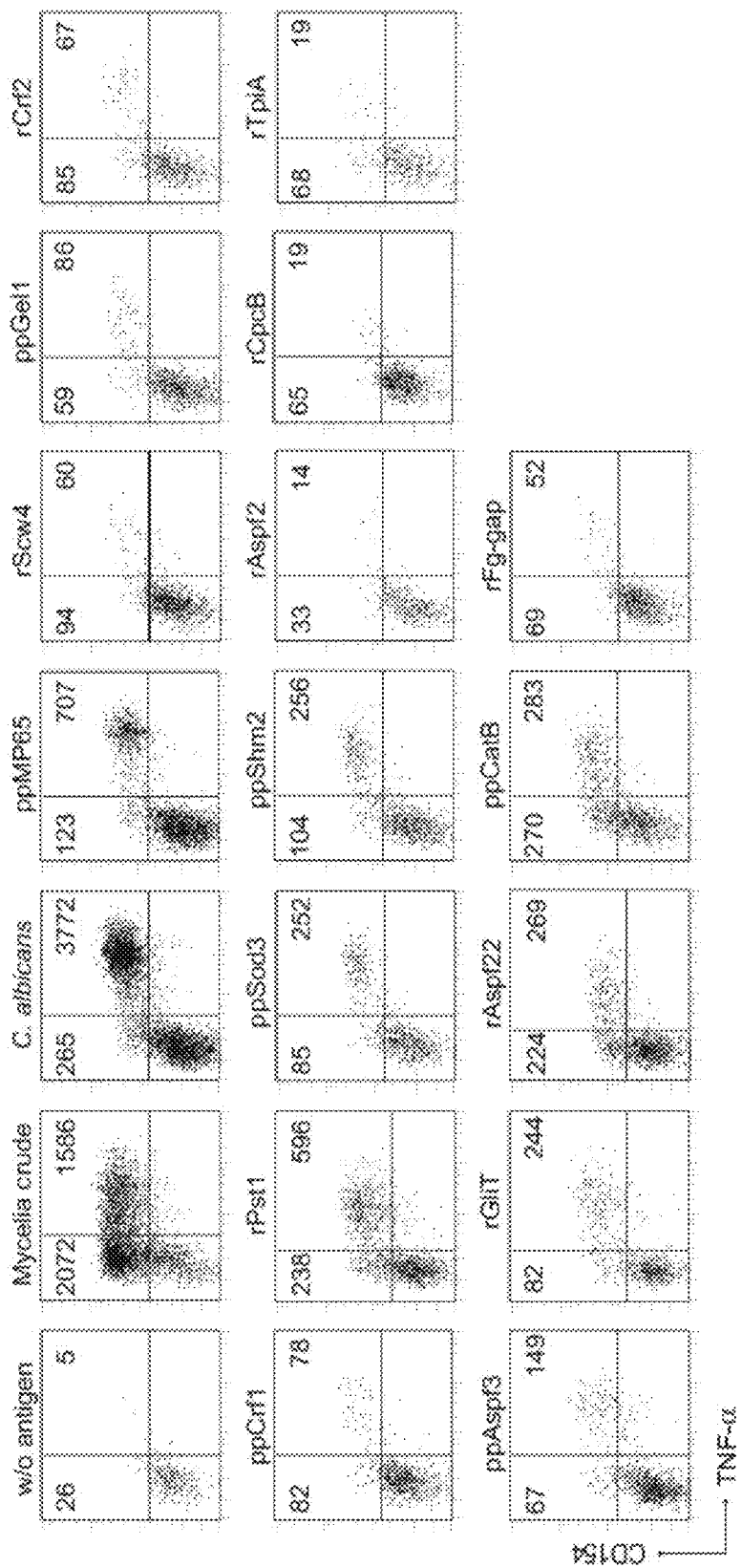
FIG. 3A-FIG. 3B show Ex vivo enumeration of CD4+ T cells reactive against single *A. fumigatus* proteins. 1×10E7 PBMCs were stimulated with *A. fumigatus* crude mycelia lysate, *C. albicans* lysate and MP65 as control antigens, or single *A. fumigatus* proteins as indicated. CD154+ cells were enriched and stained intracellularly for cytokine expression.
Figure 3B:
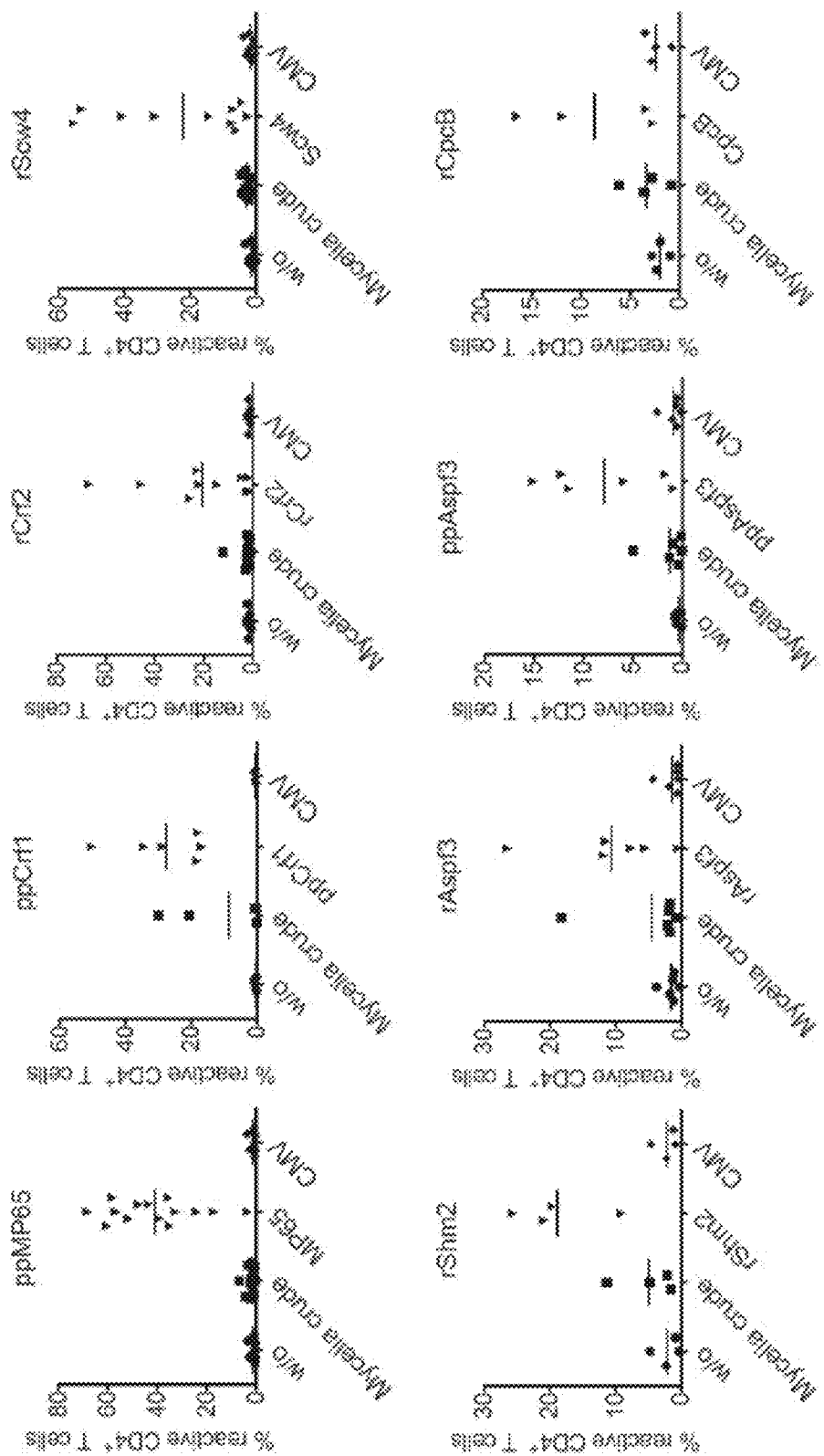

The specificity of the ex vivo detected single protein-reactive CD154+ T cells was confirmed by expansion and re-stimulation of specific T cell lines (FIG. 3B). To this end PBMC were stimulated with the proteins indicated in the FIG. 3B for 7 hours. ppMP65 is a control peptide pool of the protein MP65 of C. albicans. CD154+ cells were isolated, subsequently expanded for 3 weeks and tested for specificity via antigen re-stimulation (MP65, whole Aspergillus lysate, CMV lysate or the A. fumigatus single protein used for initial isolation of the cells). Percentage of reactive cells among CD4+ lymphocytes are shown for several donors, as determined by CD154 and TNF-α expression.

Figure 3C:
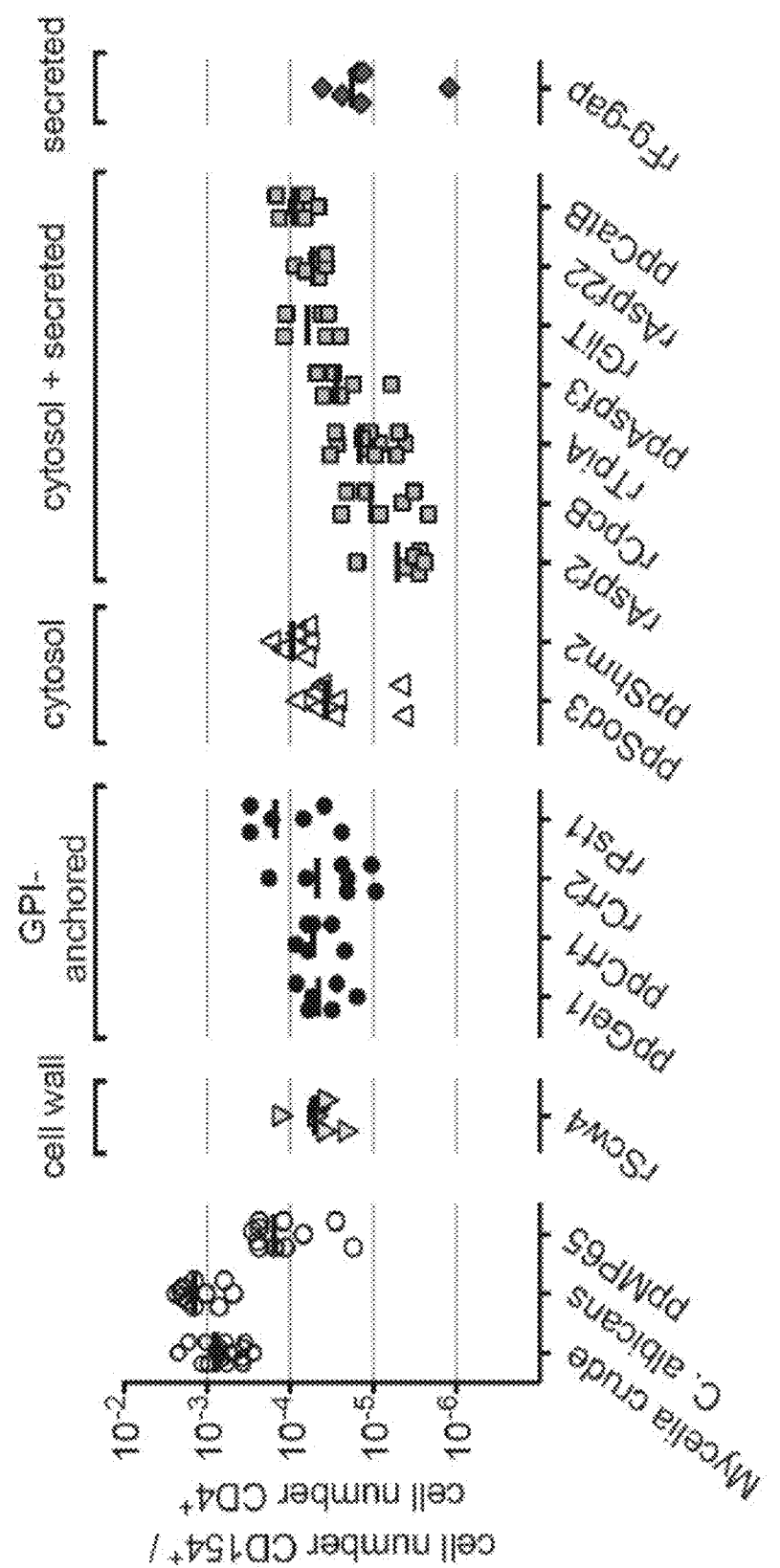
(FIG. 3C) Enumeration of reactive CD4+ T cells in several donors. The total number of CD154+ cells obtained after enrichment was normalized to the total number of CD4+ cells applied to the column. Background enriched from the non-stimulated control was subtracted. pp=peptide pool; r=recombinant protein FIG. 4. Combined characterization of frequency, phenotype and function enables classification of antigenic proteins.

Interestingly, the T cell responses against the different proteins were quite variable with frequencies ranging from 1.2×10E-6 to 3.1×10E-4 (FIG. 3C) and showed strong intra- and inter-donor variability (FIG. 3A, C). As expected, this indicates an overall diverse repertoire of A. fumigatus-reactive CD4+ T cells, probably due to different exposure and/or HLA-restriction. The subcellular location of the proteins did not result in a clear-cut phenotypic/functional characteristic of the resulting T cell response, although a trend towards a strong reactivity against membrane-associated proteins was observed.

Example 5

Figure 4:
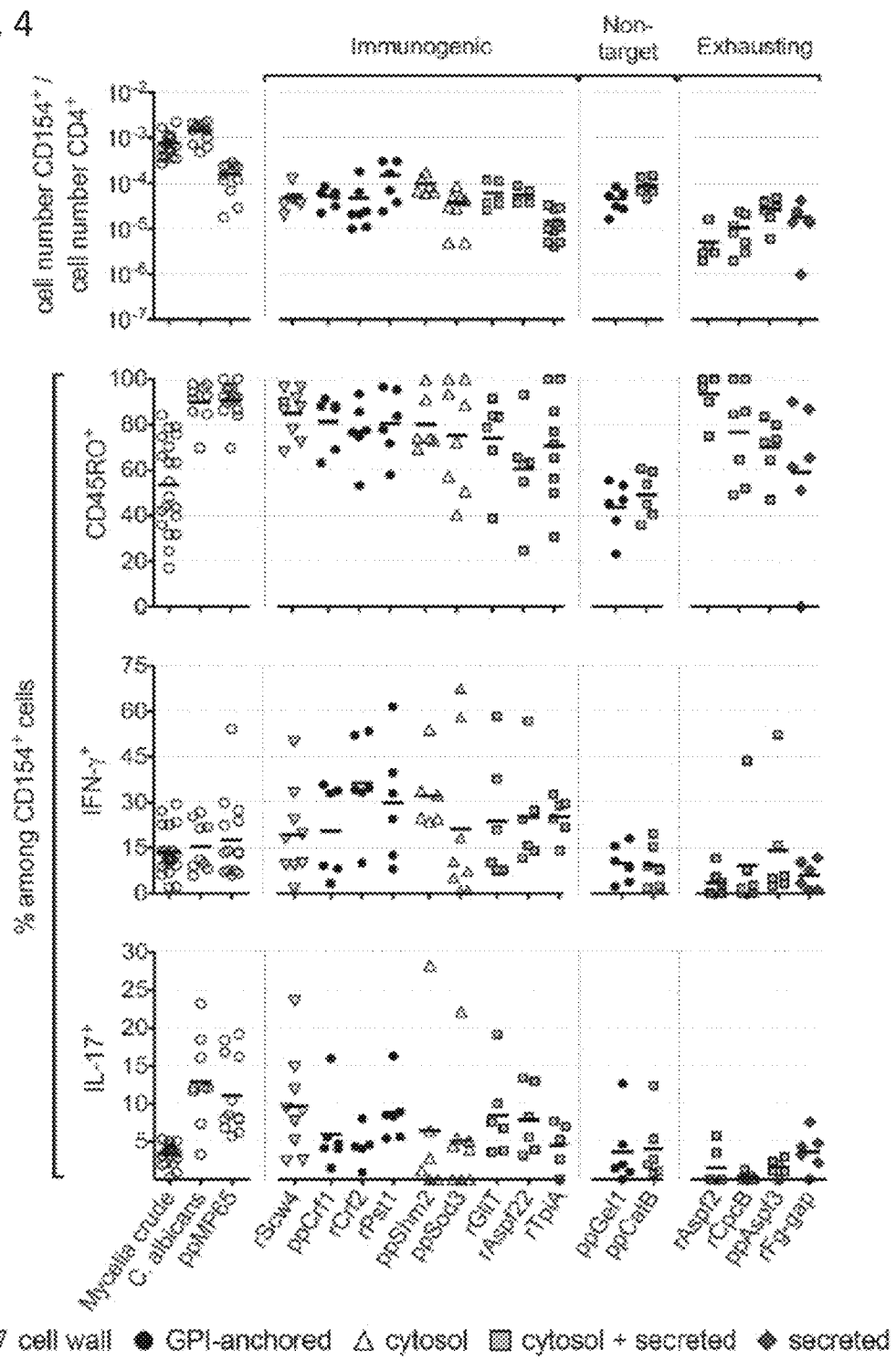

Integration of Phenotypic and Functional Markers of Specific T Cells Allows Classification of Antigenic Proteins Since our method allows multi-parameter characterization of very rare single A. fumigatus protein-specific T cells we integrated cytokine production, as well as phenotypic T cell markers, into our further analyses (FIG. 4). The combination of frequencies, naive/memory distribution and effector cytokine production allowed classification of the fungal proteins into three groups: "Immunogenic" proteins are characterized by high overall T cell frequencies, mainly memory type cells and high IFN-γ and/or IL-17 production. In contrast, "exhausting" proteins were classified due to their low to intermediate overall frequencies, and lack of effector cytokine production, although the majority of cells had a clear memory phenotype. These properties are indicative for deletion and/or anergy of specific T cells. These two groups with obvious immune reactivity in vivo contrast with the third group, which we termed "non-target" proteins, since they induce high overall T cell frequencies, but strikingly a large proportion of the cells is still in the naive state and also lacks effector cytokine production. This indicates that no immune reactivity is induced in vivo. Interestingly, the reactivity against the mycelia crude lysate as shown in FIG. 4 is also characterized by a high frequency of naive T cells and rather low effector cell frequencies, when compared to the immunogenic protein group, suggesting that a large fraction of the fungal proteins actually belong to the exhausting or non-target group.

Example 6

A. fumigatus-Specific Tcon and Treg Recognize the Same Antigens

Figure 5A:
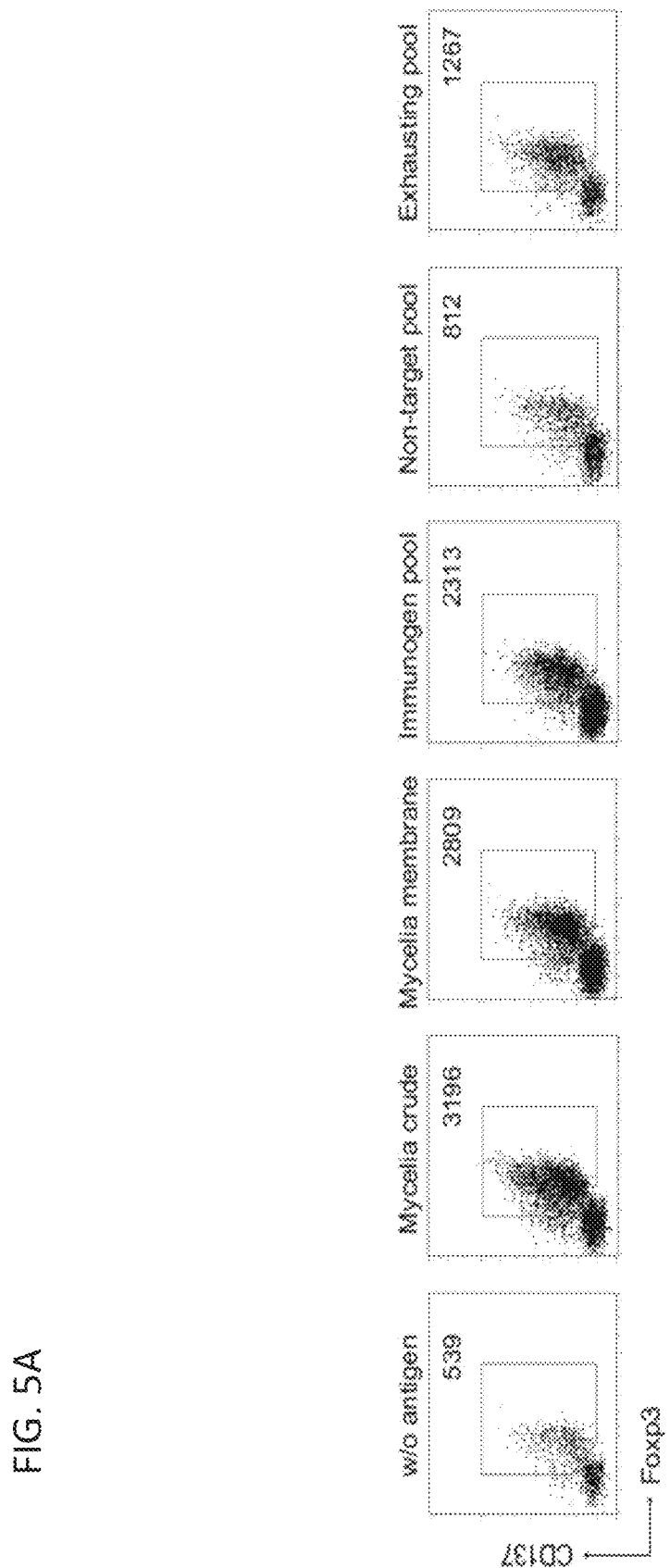
Figure 6:
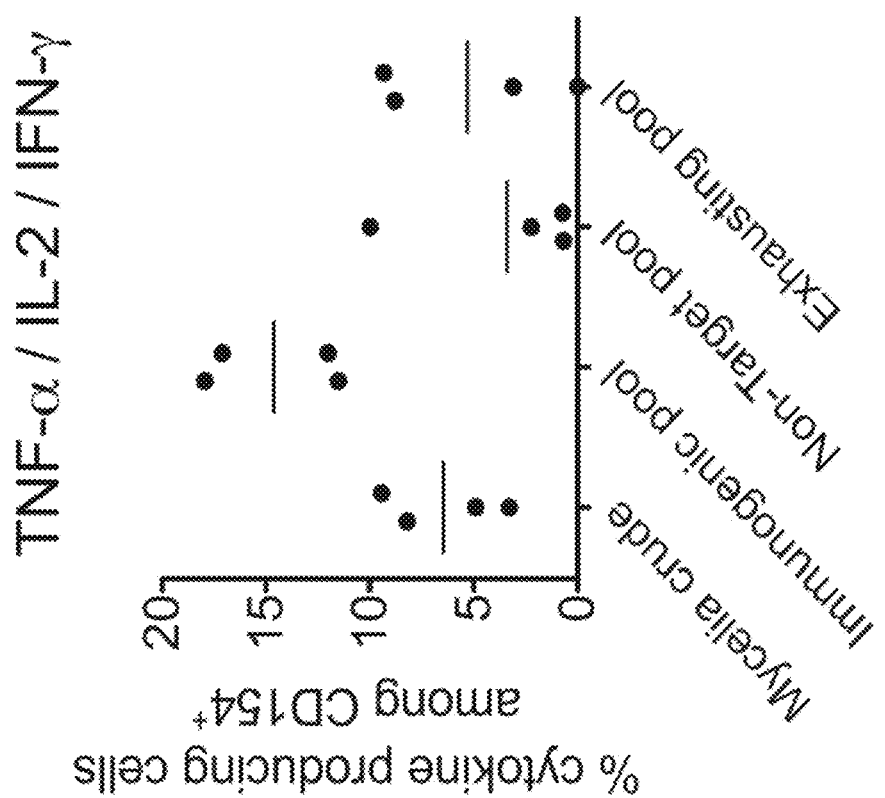
FIG. 6 shows assessment of polyfunctional cytokine induction by immunogenic, non-target or exhausting proteins.

We recently demonstrated that A. fumigatus surprisingly generates a strong Treg response in vivo, which even exceeds conventional memory T cells (Tmem) (Bacher, P. et al, Mucosal Immunol. 2013). We therefore analyzed whether the same or different antigens are recognized by A. fumigatus-specific Tmem and Treg. To this end, the single proteins were pooled according to our previous classification into a immunogenic group, containing proteins with the highest reactivity (Scw4, Crf1, Crf2, Pst1 and Shm2) as well as a non-target (Ge11, CatB) and exhausting (Aspf2, Aspf3, CpcB, Fg-Gap) group and used for stimulation in comparison to the mycelia crude lysate or the mycelia membrane fraction. CD137 which is expressed by Treg after 6 hours of stimulation was used together with CD154 enrichment to differentiate between Treg (CD137+ CD154−) and Tcon (CD137− CD154+) (Bacher, P. et al, Mucosal Immunol. 2013; Schoenbrunn, A., et al, J Immunol 2012). As shown in FIGS. 5A and B the Treg response mirrored the response of the Tcon, in that a high reactivity of specific CD137+ Treg was found in response to the A. fumigatus crude lysate, as well as the membrane fraction and the immunogenic protein pool. Again, the majority of reactive CD154+ Tcon against the immunogenic and exhausting protein pools displayed a memory phenotype, whereas a larger proportion against the non-target pool was still in the naive state (FIG. 5C). This results in an equally high Treg to Tmem ratio for all fractions (FIG. 5D), indicating that A. fumigatus-specific Treg and Tmem are directed against the same target antigens and that the A. fumigatus-specific T cell response is balanced by specific Treg cells.

REFERENCES

Bacher, P., C. Schink, J. Teutschbein, O. Kniemeyer, M. Assenmacher, A. A. Brakhage, and A. Scheffold. 2013.

Antigen-reactive T cell enrichment for direct, high-resolution analysis of the human naive and memory Th cell repertoire. J Immunol 190: 3967-3976.

Bacher, P., 0. Kniemeyer, A. Schonbrunn, B. Sawitzki, M. Assenmacher, E. Rietschel, A. Steinbach, O. A. Comely, A. A. Brakhage, A. Thiel, and A. Scheffold. 2013. Antigen-specific expansion of human regulatory T cells as a major tolerance mechanism against mucosal fungi. Mucosal Immunol. 2013

Frentsch, M., O. Arbach, D. Kirchhoff, B. Moewes, M. Worm, M. Rothe, A. Scheffold, and A. Thiel. 2005. Direct access to CD4+ T cells specific for defined antigens according to CD154 expression. Nat Med 11: 1118-1124.

Schoenbrunn, A., M. Frentsch, S. Kohler, J. Keye, H. Dooms, B. Moewes, J. Dong, C. Loddenkemper, J. Sieper, P. Wu, C. Romagnani, N. Matzmohr, and A. Thiel. 2012. A converse 4-1BB and CD40 ligand expression pattern delineates activated regulatory T cells (Treg) and conventional T cells enabling direct isolation of alloantigen-reactive natural Foxp3+Treg. J Immunol 189: 5985-5994.

Shi, L. N., F. Q. Li, M. Huang, J. F. Lu, X. X. Kong, S. Q. Wang, and H. F. Shao. 2012. Immunoproteomics based identification of thioredoxin reductase GliT and novel *Aspergillus fumigatus* antigens for serologic diagnosis of invasive aspergillosis. BMC Microbiol 12: 11.

Vödisch, M., D. Albrecht, F. Lessing, A. D. Schmidt, R. Winkler, R. Guthke, A. A. Brakhage, and 0. Kniemeyer. 2009. Two-dimensional proteome reference maps for the human pathogenic filamentous fungus *Aspergillus fumigatus*. Proteomics 9: 1407-1415.

Sequences

```
                                              SEQ ID NO: 1
Aspergillus fumigatus cell wall glucanase
Scw4 (protein)
MRLKVNLLAL LLAYRSAAHP HVGHRRNAEH DVKPKEQVIV

WVDHAGHTIG IEHKHQTPTA TFKSSPTELP LLPNTDNIIP

DNPLPKLTVE VPELNTNRGP RFGITYSPYT SHGTCKTFDQ

INQDIEHLRH HAFIRIYGID CDQTKLVTQA SRQHGLKVFA

GVFDLHNFPD SLHYIRDAAT AAGGDWSIFH TIAIGNELVN

KGQNKPADVV NAVNTARGIL RGAGYQGPVV TVDTFSVMLQ

HPELCAASDY CAANCHAFFD NNQLPETAGE YALDKARRIS

AAAGGKKTVI TESGWPHAGQ PNGRAVPSPE NQKKAIASLR

KAFADDPDLV LFTAFDDLWK SDNQWTFGAE RFWGIQDMGR

EREREQDRE

SEQ ID NO: 2
Aspergillus fumigatus GPI-anchored cell wall
protein Pst1 (protein)
MRPLFFCLLL ALRLVAADDG EESDSNPRCN TDVNIASQAD

ADSIASCHTV RGSVTMASSV SGAVNLHGVE TIQGPLTARG

ASDLSALIAS DLKTITGTLT VANNDALNQI SMSNLQTVGG

DFKVENNRNL KDLSLSDLDE IRGGVTVSDL TRRRISLSNL

DTVWGPTVIH SSGTFNCSSL DSKLSGEDRV FQSSYSCTTG

KSNKSSGSDG LSTGAKAGIA VAVVIVVLLI LFFLWLLIRR

RKRQQNRRTE KTVTDAISQ TPAPTGHESN TEKLTSTLTP

PQEDVERGIP RKPVSPPPAA DRRSSVPASL LPGSGRLSVP

VSLLPGSNPS VSSASASHRR VTSDPSLFLH HIAPSAPQPP

PSEIDVPMLD SGNVYEVGND RTRPQTPIYE LDGGGMSNHQ

QPIHRE

SEQ ID NO: 3
Aspergillus fumigatus serine hydroxymethyl-
transferase Shm2 (protein)
MATYALSQAH REQMEKSLVD SDPEIAQIME KEIQRQRESI

LLIASENVTS RAVFDALGSP MSNKYSEGYP GARYYGGNQH

IDAIELTCQA RALKAFNLDP EKWGVNVQCL SGSPANLEVY

QALMRPHDRL MGLDLPHGGH LSHGYQTPSR KISAVSTYFE

TFPYRVNTET GIIDYDTLEA NAELYRPKCL VAGTSAYCRL

IDYGRMRKIA DKVGAYLIVD MAHISGLVAA GVIPSPFEYA

DVVTTTTHKS LRGPRGAMIF FRKGVRSTDP KTGKEIMYDL

EGPINFSVFP GHQGGPHNHT ITALAVALKQ AATPEFRQYQ

EQVLKNAKAL EVEFKALGHK LVSDGTDSHM VLLDLRPKGL

DGARVEAVLE QINIACNKNS IPGDKSALTP CGIRIGTPAM

TSRGMSEEDF KRVARYIDQV INLCKSIQAD LPKEANKLKD

FKAKVASGSV PEILALRKEV AEWASTYPLP V

SEQ ID NO: 4
Aspergillus fumigatus thioredoxin
reductase GliT (protein)
MSIGKLLSNG ALLVDVLIIG AGPAGLSTAT GLARQLHTAV

VFDSGVYRNA KTQHMHNVLG WDHRNPAELR AAGRADLTTR

YSTIQFQNST IEAIRQVETN QLFEARDNEG HSWYGRKVVL

ATGVRDIPLD IEGYSECWAN GIYHCLFCDG YEERGQETVG

VLALGPIANP ARALHLARMA LRLSESVTIY TNGNEQLAKE

IQQAAEESPV GASGLKFEAR PIRRFEKGDV AKTVIVHLGE

SESKTEGFLV YNPQTEVNGP FAKQLALNMT EGGDILTTPP

FYETSVPGVF AVGDCATPLK AVTPAVSMGS LAAGGLVAQL

QAQALPEFRL DQEL

SEQ ID NO: 5
Aspergillus fumigatus triosephosphate
isomerase TpiA (protein)
MPRQFFVGGN FKMNGVTDTI TSIVKNLNEA KLDPSVEVVI

SPSALYLLLA RQAADPKIGV AAQNVFDKPN GAFTGEISVE

QLKDAKIDWV IIGHSERRVI LKETDEFIAR KTKAAIDGGL

NVILCIGETL EEREAGKTID VVRRQLTAVA KDLSKEQWQK

VVIAYEPVWA IGTGKVATTE QAQEVHAAIR KWLSDDVSAE

ASENVRIIYG GSVSEKNCRD LAKQPDVDGF LVGGASLKPA

FVEIVNARL
```

The invention claimed is:

1. A method for detecting, isolating and/or analyzing *Aspergillus fumigatus*-specific CD4+T cells, the method comprising:
   a) adding to a sample comprising T cells at least one purified in-vivo-target antigen of *Aspergillus fumigatus*, wherein said at least one in-vivo-target antigen reveals an immune reactivity characterized by
      i) the in vivo existence of antigen-specific T cells comprising more than 60% memory T cells, and
      ii) said antigen-specific T cells further comprise T cells able to produce IFN-gamma upon stimulation at a frequency between 15% and 80% and/or IL17 upon stimulation at a frequency between 5% and 30%
   b) detection, isolation and/or analysis of activated *Aspergillus fumigatus*-specific CD4+T cells,
   wherein said at least one in vivo target antigen is selected from the group consisting of Scw4, Pst1, Shm2, GliT and TpiA.

2. The method according to claim 1, wherein said *Aspergillus fumigatus* specific CD4+T cells comprise regulatory T cells, memory T cells and naïve T cells.

3. The method according to claim 1 comprising the additional step of enrichment of reactive T cells from a sample comprising T cells before adding the at least one in-vivo-target-antigen.

4. The method according to claim 3, wherein enrichment of said reactive T cells is performed by
   i) fluorescently or magnetically labeling of one or more activation markers of said reactive T cells, wherein said activation markers are selected from the group consisting of CD154, CD137, IL-2, IL-4, IL-5, IL-9, IL-13, Il-17, IL-22, IFN-gamma, TNF-alpha, CD134, CD69, and TGF-beta latency associated peptide (LAP)
   ii) enriching the labeled cells of step i) via flow cytometry or magnetic cell separation methods.

5. The method according to claim 1 comprising the additional step of expansion of activated *Aspergillus fumigatus*-specific CD4+T cells.

6. The method according to claim 1, wherein said at least one in-vivo-target antigen is a full length protein, a fragment thereof, a peptide, a peptide pool, or fragments thereof.

* * * * *